United States Patent
Voorhees et al.

(10) Patent No.: US 12,370,087 B2
(45) Date of Patent: *Jul. 29, 2025

(54) LASIK FLAP CUTTING PATTERNS INCLUDING INTRASTROMAL POCKET FOR BUBBLE MANAGEMENT

(71) Applicant: AMO Development, LLC, Irvine, CA (US)

(72) Inventors: Andrew Voorhees, Sunnyvale, CA (US); Harvey Liu, Fremont, CA (US); Hong Fu, Pleasanton, CA (US); Alireza Malek Tabrizi, Fremont, CA (US); Nima Khatibzadeh, San Jose, CA (US); Deepali Mehta-Hurt, Newark, CA (US); Cynthia Villanueva, San Jose, CA (US); James Hill, Santa Ana, CA (US); Alisyn Facemire, Virginia Beach, VA (US)

(73) Assignee: AMO Development, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/439,724

(22) Filed: Feb. 12, 2024

(65) Prior Publication Data

US 2024/0180746 A1 Jun. 6, 2024

Related U.S. Application Data

(63) Continuation of application No. 17/457,419, filed on Dec. 2, 2021, now Pat. No. 11,903,878.
(Continued)

(51) Int. Cl.
*A61F 9/008* (2006.01)
*A61B 18/00* (2006.01)
*A61B 18/20* (2006.01)

(52) U.S. Cl.
CPC ...... *A61F 9/00836* (2013.01); *A61B 2018/00779* (2013.01); *A61B 2018/20353* (2017.05);
(Continued)

(58) Field of Classification Search
CPC ........ A61F 9/00836; A61F 2018/20355; A61F 2018/20353; A61F 2018/00779; A61F 2018/00872; A61F 2018/00897
See application file for complete search history.

(56) References Cited

U.S. PATENT DOCUMENTS

| 8,425,499 B2 | 4/2013 | Donitzky et al. |
| 8,491,577 B2 | 7/2013 | Kittelmann et al. |

(Continued)

FOREIGN PATENT DOCUMENTS

| CN | 101287418 A | 10/2008 |
| CN | 102740813 A | 10/2012 |

(Continued)

OTHER PUBLICATIONS

Courtin R., et al., "Opaque Bubble Layer Risk Factors in Femtosecond Laser-assisted LASIK," Journal of Refractive Surgery, Sep. 2015, vol. 31 (9), pp. 608-612.
(Continued)

*Primary Examiner* — Lynsey C Eiseman
*Assistant Examiner* — Skylar Lindsey Christianson

(57) ABSTRACT

A method implemented in an ophthalmic surgical laser system that employs a resonant scanner, scan line rotator, and XY- and Z-scanners, for forming a corneal flap in a patient's eye with improved bubble management during each step of the flap creation process. A pocket cut is formed first below bed level, followed by the bed connected to the pocket cut, then by a side cut extending from the bed to the anterior corneal surface. The pocket cut includes a pocket region located below the bed level and a ramp region
(Continued)

connecting the pocket region to the bed. The bed is formed by a hinge cut and a first ring cut at lower laser energies, followed by a bed cut and then a second ring cut, which ensures that any location in the flap bed is cut twice to minimize tissue adhesion. The side cut is formed by multiple side-cut layers at different depths which are joined together. All cuts are formed by scanning a laser scan line generated by the resonant scanner.

18 Claims, 13 Drawing Sheets

Related U.S. Application Data

(60) Provisional application No. 63/121,073, filed on Dec. 3, 2020.

(52) U.S. Cl.
CPC ............ *A61B 2018/20355* (2017.05); *A61F 2009/00872* (2013.01); *A61F 2009/00897* (2013.01)

(56) References Cited

U.S. PATENT DOCUMENTS

| | | | |
|---|---|---|---|
| 8,715,272 | B2 | 5/2014 | Donitzky et al. |
| 9,138,348 | B2 | 9/2015 | Wolfel |
| 9,737,438 | B2 | 8/2017 | Rathjen |
| 9,789,003 | B2 | 10/2017 | Martin |
| 9,943,442 | B2 | 4/2018 | Krause et al. |
| 10,105,262 | B2 | 10/2018 | Papastathopoulos et al. |
| 2007/0219542 | A1 | 9/2007 | Yahagi |
| 2008/0114386 | A1 | 5/2008 | Iliakis et al. |
| 2014/0121654 | A1 | 5/2014 | Loden |
| 2015/0190282 | A1 | 7/2015 | Bor et al. |
| 2016/0008173 | A1* | 1/2016 | Krause ............... A61F 9/00836 606/5 |
| 2016/0089270 | A1 | 3/2016 | Fu |
| 2016/0374857 | A1 | 12/2016 | Fu et al. |
| 2017/0367883 | A1* | 12/2017 | Malek Tabrizi .... A61F 9/00827 |
| 2018/0110648 | A1 | 4/2018 | Fu et al. |
| 2018/0193196 | A1 | 7/2018 | Bergt et al. |
| 2019/0015253 | A1 | 1/2019 | Rathjen |
| 2019/0083308 | A1 | 3/2019 | Rathjen |
| 2019/0110926 | A1 | 4/2019 | Malek Tabrizi et al. |

FOREIGN PATENT DOCUMENTS

| | | |
|---|---|---|
| CN | 104039284 A | 9/2014 |
| CN | 104540482 A | 4/2015 |
| WO | 03082146 A2 | 10/2003 |
| WO | 2014135218 A1 | 9/2014 |
| WO | 2014143580 A1 | 9/2014 |
| WO | 2016209312 A1 | 12/2016 |

OTHER PUBLICATIONS

Fawzy N.F., Femto-Assisted Enhancement After Micro-keratome Initial Cut, The "Ring Cut", 2019, 32 pages.

Jhanji V., et al., "Conventional Versus Inverted Side-cut Flaps for Femtosecond Laser-Assisted LASIK: Laboratory and Clinical Evaluation," Journal of Refractive Surgery, 2017, vol. 33 (2), pp. 96-103.

\* cited by examiner

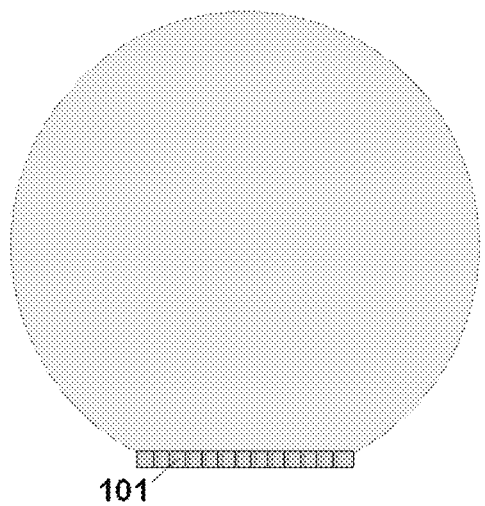
Fig. 2A1
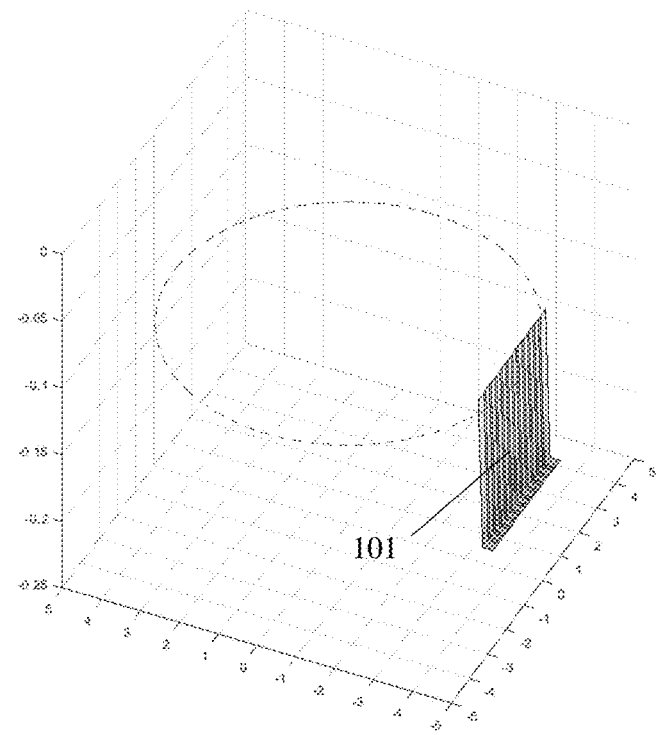
Fig. 2B1
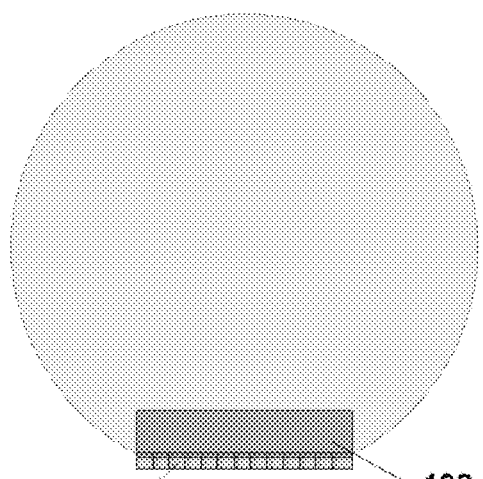
Fig. 2A2
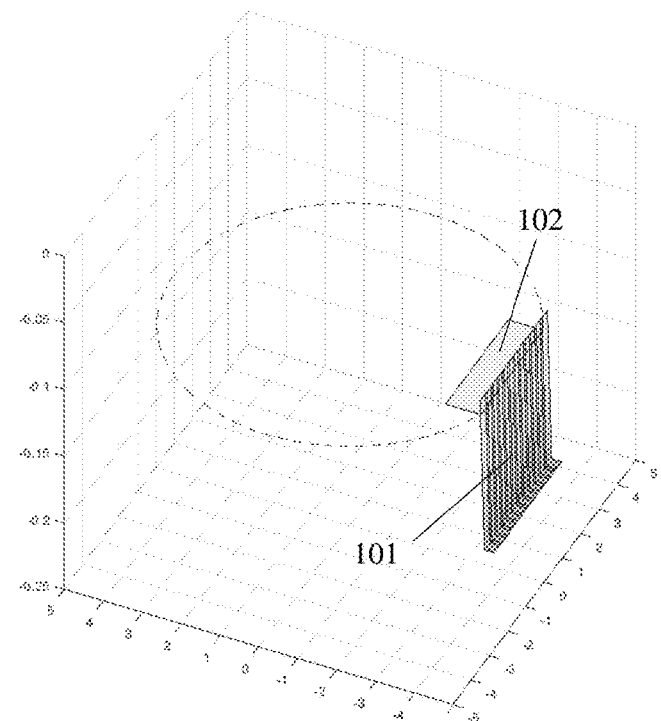
Fig. 2B2

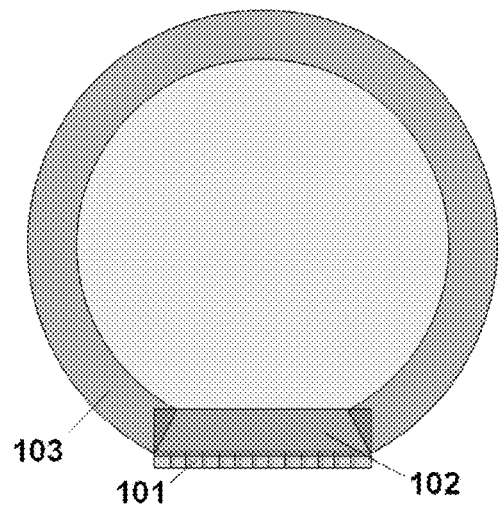
Fig. 2A3
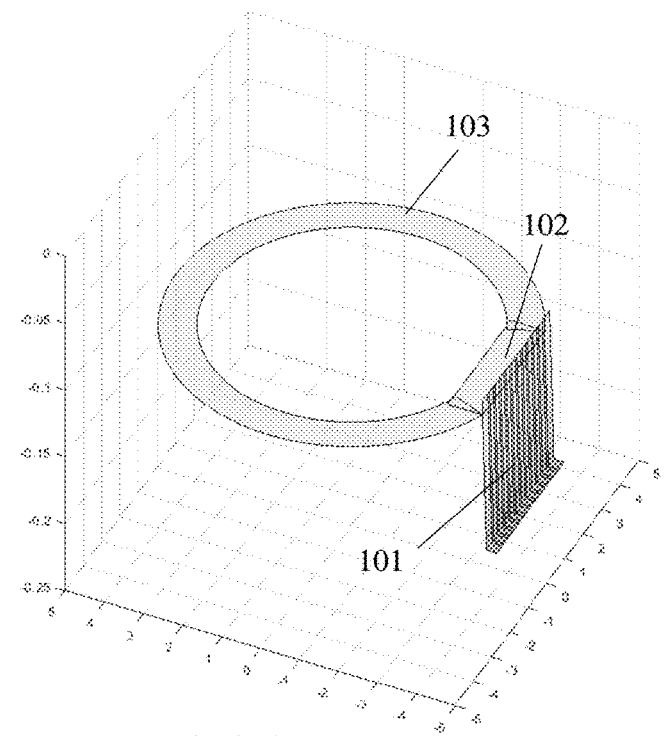
Fig. 2B3
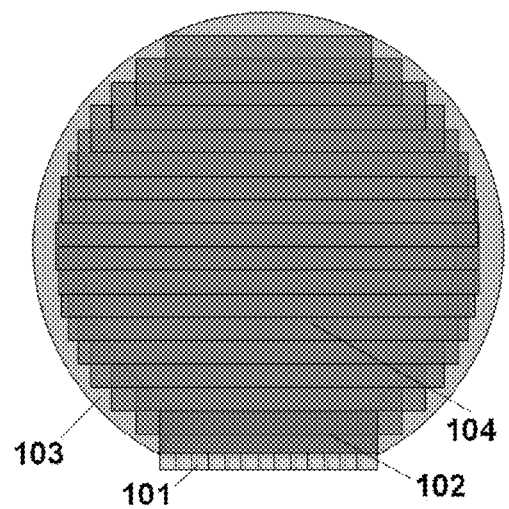
Fig. 2A4
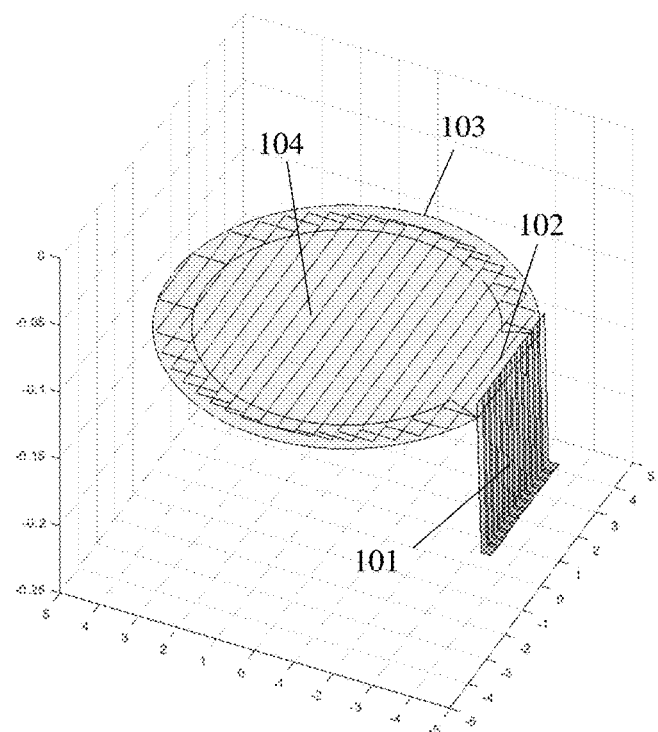
Fig. 2B4

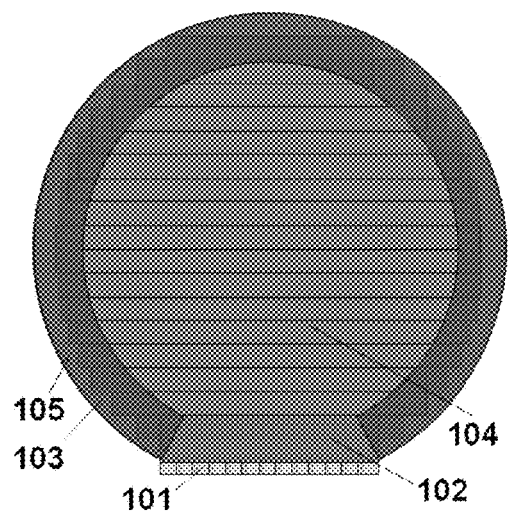
Fig. 2A5
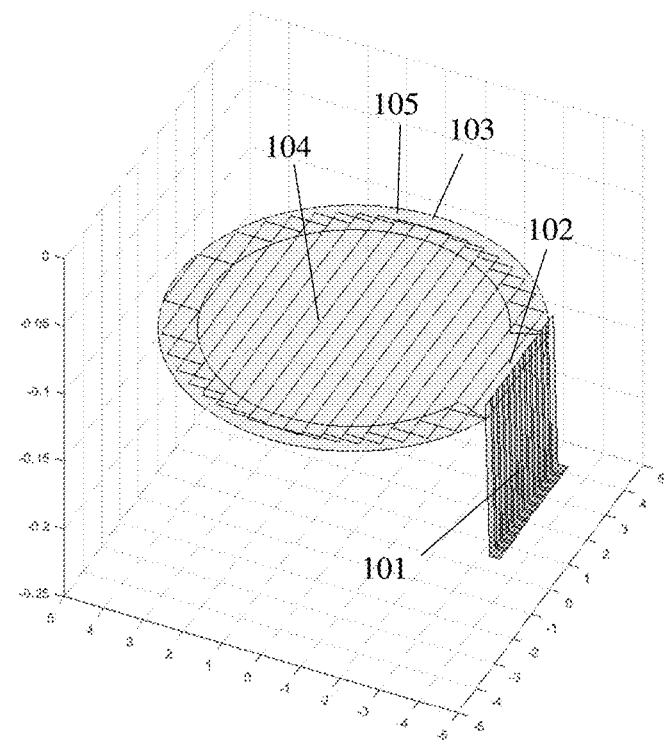
Fig. 2B5
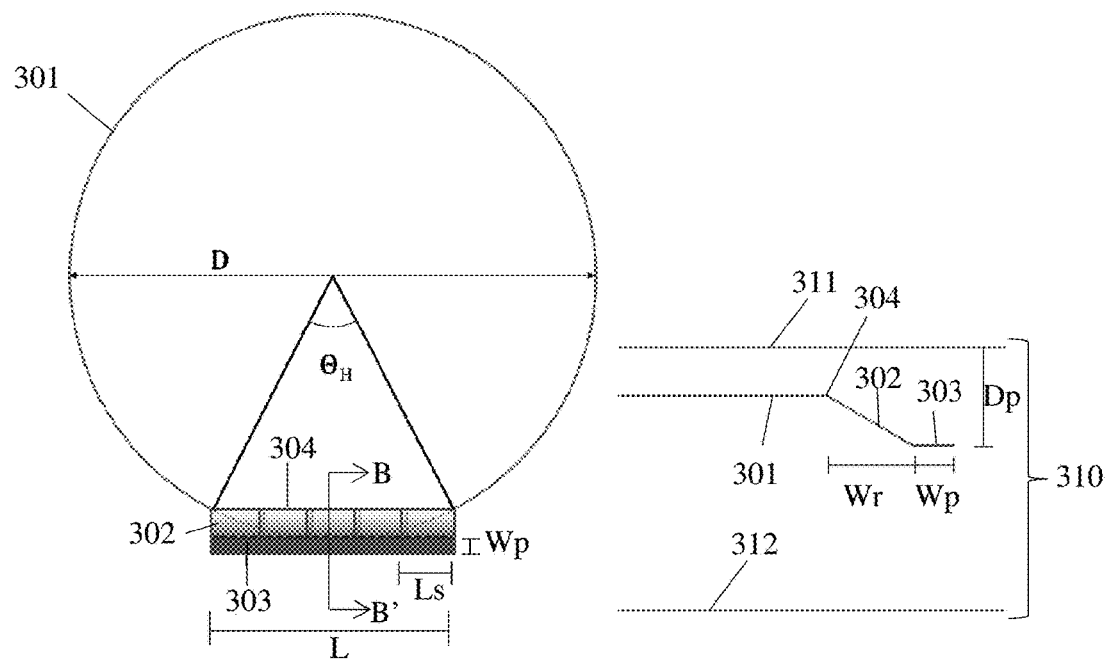
Fig. 3

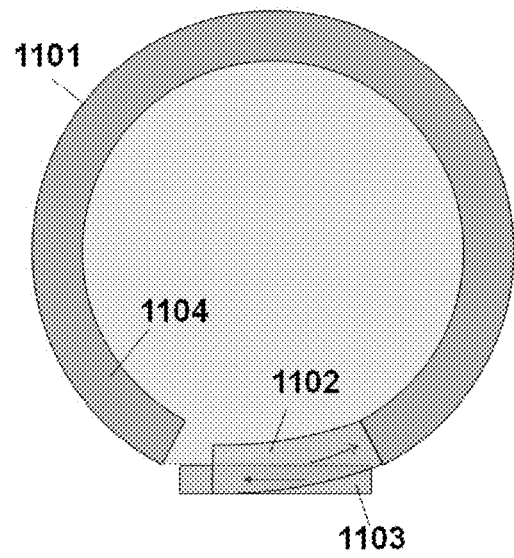
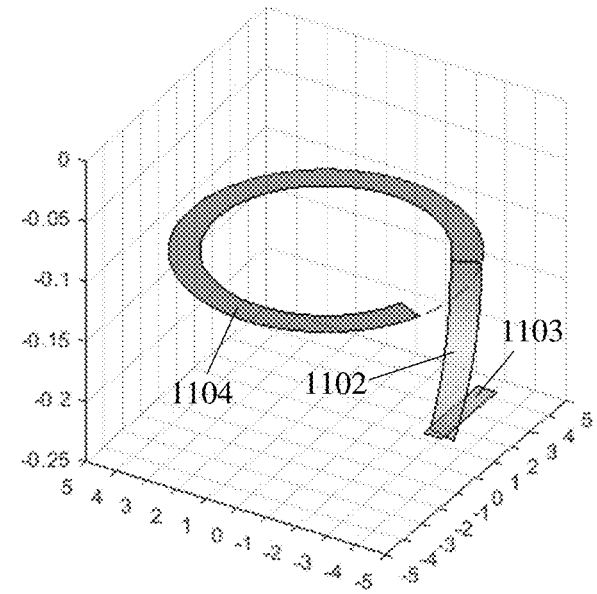
Fig. 11A                    Fig. 11B
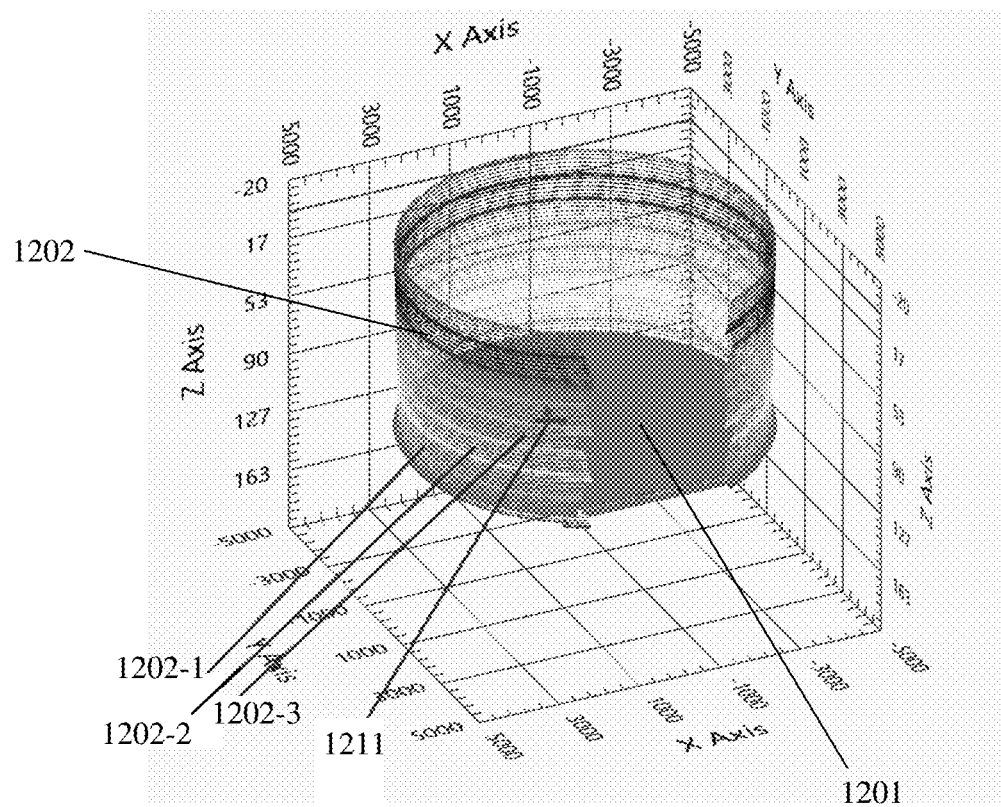
Fig. 12

LASIK FLAP CUTTING PATTERNS INCLUDING INTRASTROMAL POCKET FOR BUBBLE MANAGEMENT

CROSS REFERENCE TO RELATED APPLICATIONS

This application is a continuation of U.S. patent application Ser. No. 17/457,419, filed Dec. 2, 2021, which claims priority to U.S. Provisional Patent Application No. 63/121,073, filed on Dec. 3, 2020, the entire contents of which are hereby incorporated by reference.

BACKGROUND OF THE INVENTION

Field of the Invention

This invention relates to ophthalmic laser surgeries, and in particular, it relates to flap cutting in LASIK (laser-assisted in situ keratomileusis) surgery using an ultrafast resonant scanning femtosecond laser.

Description of Related Art

Femtosecond lasers are used to cut flaps in the corneal stroma as the first step of LASIK (laser-assisted in situ keratomileusis) surgeries. A flap is typically formed by a bed cut which is parallel to the anterior corneal surface and a vertical side cut around the periphery of the bed cut expect for an uncut hinge region.

When using femtosecond lasers to cut a flap in the corneal stroma as a part of a LASIK procedure, the interaction of the laser pulses with the tissue can sometimes create excessive gas bubbles which can interfere with the continued cutting of the tissue, creating tissue bridges and rough bed cut surfaces. FIG. 14 schematically illustrates a flap bed cut being formed in the tissue and a gas bubble that was created by the laser during a previous laser raster scan, showing the gas bubble blocking the current scan pass. This could lead to a region of uncut tissue. Gas bubbles can also shadow the laser beam for the subsequent segments of the flap cut, creating tissue bridges.

SUMMARY

The present invention is directed to a method and related apparatus for incising a corneal flap in LASIK surgery that substantially obviates one or more of the problems due to limitations and disadvantages of the related art.

Embodiments of this invention provide flap cutting patterns including intrastromal pockets that can be implemented with a resonant scanning femtosecond laser. These flap cutting patterns will allow for gas bubbles to collect and vent posterior to and outside of the flap bed cut.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method implemented in an ophthalmic surgical laser system for incising a cornea of a patient's eye to form a corneal flap, the method including: controlling a laser delivery system of the ophthalmic surgical laser system to deliver a pulsed laser beam to the cornea; controlling a high frequency scanner of the ophthalmic surgical laser system to scan the pulsed laser beam back and forth to form a laser scan line; and controlling a scan line rotator, an XY-scanner and a Z-scanner of the ophthalmic surgical laser system to move the laser scan line in the cornea to form the corneal flap, including forming a pocket cut, forming a bed of the flap, and forming a side cut of the flap, wherein the bed is located in a horizontal plane at a first depth from an anterior corneal surface, the bed defining a hinge line, wherein the side cut extends from the bed upwards to the anterior corneal surface to form a side of the flap, the side cut surrounding an entire periphery of the bed except the hinge line, and wherein the pocket cut includes a ramp region and a pocket region connected to each other, wherein the pocket region is located at a second depth from the anterior corneal surface which is deeper than the first depth, wherein the pocked region has a shape of a rectangle, or multiple rectangles joined to each other, or a segment of a ring in a top view, and wherein the ramp region extends between the first depth and the second depth and is connected to both the bed and the pocket region.

In preferred embodiments, the pocket cut is formed first, the bed is formed after the pocket cut, and the side cut is formed after the bed.

In another aspect, the present invention provides a method implemented in an ophthalmic surgical laser system for incising a cornea of a patient's eye to form a corneal flap, the method including: controlling a laser delivery system of the ophthalmic surgical laser system to deliver a pulsed laser beam to the cornea; controlling a high frequency scanner of the ophthalmic surgical laser system to scan the pulsed laser beam back and forth to form a laser scan line; and controlling a scan line rotator, an XY-scanner and a Z-scanner of the ophthalmic surgical laser system to move the laser scan line in the cornea to form the corneal flap, including forming a bed of the flap and forming a side cut of the flap, wherein the bed is located in a horizontal plane at a first depth from an anterior corneal surface, the bed defining a hinge line, wherein the side cut extends from the bed upwards to the anterior corneal surface to form a side of the flap, the side cut surrounding an entire periphery of the bed except for the hinge line, and wherein the step of forming the bed includes: forming a hinge cut along the hinge line by scanning the laser scan line along the hinge line; forming a first ring cut along a periphery of the bed except for an area of the hinge cut by scanning the laser scan line along a circumference of the bed; forming a bed cut by scanning the laser scan line in overlapping parallel raster scan passes, the bed cut overlapping at least a part of the hinge cut and the first ring cut and covering all areas of the bed not covered by the hinge cut and the first ring cut; and forming a second ring cut overlapping the first ring cut by scanning the laser scan line along the circumference of the bed.

In preferred embodiments, the bed cut is formed after both the hinge cut and the first ring cut, and the second ring cut is formed after the bed cut. The hinge cut and the first ring cut are formed using a first laser pulse energy, and the bed but, the second ring cut, and the side cut are formed using a second laser pulse energy which is higher than the first laser pulse energy.

In another aspect, the present invention provides a method implemented in an ophthalmic surgical laser system for incising a cornea of a patient's eye to form a corneal flap, the method including: controlling a laser delivery system of the ophthalmic surgical laser system to deliver a pulsed laser beam to the cornea; controlling a high frequency scanner of the ophthalmic surgical laser system to scan the pulsed laser beam back and forth to form a laser scan line; and controlling a scan line rotator, an XY-scanner and a Z-scanner of the ophthalmic surgical laser system to move the laser scan line in the cornea to form the corneal flap, including forming a bed of the flap and forming a side cut of the flap, wherein the bed is located in a horizontal plane parallel to an anterior corneal surface of the cornea, wherein the side cut extends from the bed upwards to the anterior corneal surface to form a side of the flap, and wherein the step of forming the side cut includes forming a plurality of side cut layers in a sequence, each side cut layer extending within a depth range relative to the anterior corneal surface, wherein all except one of the plurality of side cut layers are located entirely within the cornea without reaching the anterior corneal surface, and wherein the plurality of side cut layers are aligned with each other and connect with each other to form the side cut.

In preferred embodiments, the depth ranges of adjacent side cut layers overlap each other, and the plurality of side cut layers are formed in a sequence from deeper side cut layers to shallower side cut layers. Each of the plurality of side cut layers is formed by placing the laser scan line tangent to a circumference of the side cut, moving the laser scan line in a vertical direction, simultaneously moving the laser scan line around the circumference, and simultaneously rotating the scan line to keep it tangent to the circumference.

In another aspect, the present invention provides an ophthalmic surgical laser system, which includes: a laser delivery system configured to deliver a pulsed laser beam to a cornea of a patient's eye; a high frequency scanner configured to scan the pulsed laser beam back and forth at a predefined frequency to form a laser scan line; a scan line rotator configured to rotate an orientation of the laser scan line; an XY-scanner and a Z-scanner configured to move the laser scan line in lateral and depth directions; and a controller operatively coupled to and programmed to control the scan line rotator, the XY-scanner and the Z-scanner to scan the laser scan line in the cornea to form a corneal flap, including to perform various steps in any of the above described methods.

It is to be understood that both the foregoing general description and the following detailed description are exemplary and explanatory and are intended to provide further explanation of the invention as claimed.

BRIEF DESCRIPTION OF THE DRAWINGS

FIGS. 2A1-2B5 schematically illustrate a cutting sequence in the first embodiment.

FIG. 3 schematically illustrates a flap procedure that forms a corneal flap with a pocket cut according to a second embodiment of the present invention.

FIG. 5 schematically illustrates a flap procedure that forms a corneal flap with a pocket cut according to a fourth embodiment of the present invention.

FIGS. 11A-11B schematically illustrate a flap procedure that forms a corneal flap with a pocket cut according to a tenth embodiment of the present invention.

FIG. 12 schematically illustrates a flap procedure that forms a corneal flap according to an eleventh embodiment of the present invention which employs layered side cut.

DETAILED DESCRIPTION OF PREFERRED EMBODIMENTS

Figure 15:
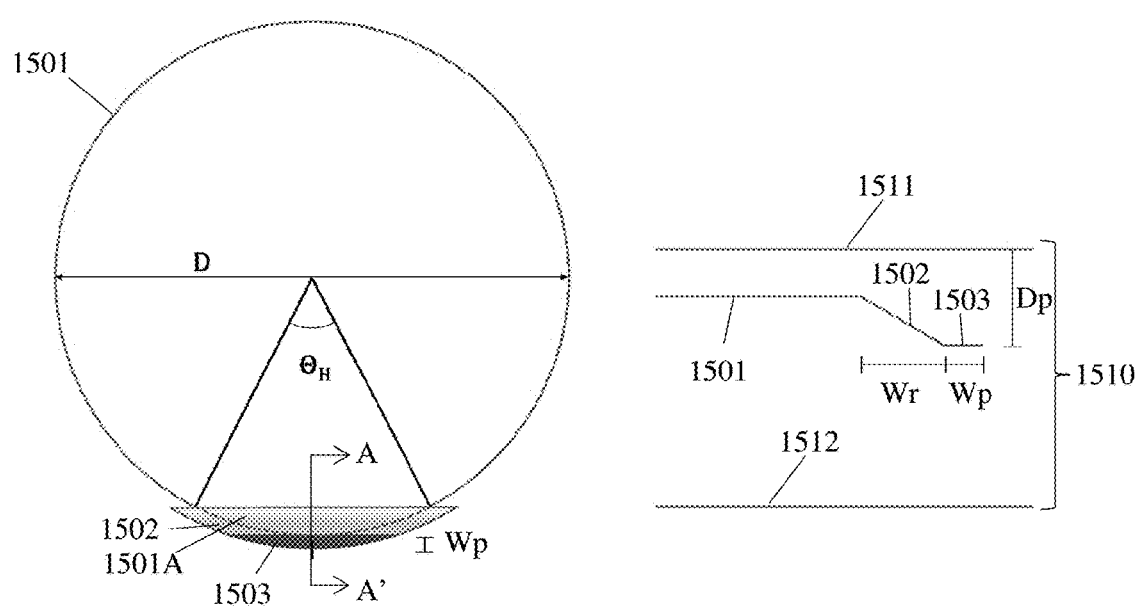
FIG. 15 schematically illustrates a flap procedure that forms a corneal flap according to a conventional technology.

A previous technique for managing gas bubble formation during bed cut uses an intrastromal pocket cut, as shown in FIG. 15 (top view and depth profile). FIG. 15 shows a flap cut formed of a bed cut 1501, which is a circular area except for an arc segment 1501A which is uncut and which serves as a hinge portion to allow the flap to be folded away and then re-placed over the stroma, a pocket cut 1502, 1503 connected to the bed cut at the hinge, including a ramp region 1502 and a pocket region 1503, and a vertically extending side cut (also designated by the reference symbol 1501 in the top view, not shown in the depth profile) located around the periphery of the bed cut except for the hinge portion. Both the ramp region 1502 and the pocket region 1503 are arc segments (area bound by an arc and the straight line connecting two ends of the arc) in the top view. In terms of the cutting sequence, the first cut made is the pocket region 1503 which is outside the radius of the bed cut 1501. Next the ramp region 1502 is made which will eventually connect the pocket region to the bed cut. The bed cut 1501 and side cut are made after the pocket cut. In a particular example (see FIG. 15), the flap diameter D is 9.0 mm, the pocket width Wp is 250 μm, and the hinge angle $\Theta_H$ is 55°. FIG. 15 also shows a depth profile 1510 through the center of the hinge as indicated by arrows A-A', showing the anterior corneal surface 1511, posterior corneal surface 1512, a part of the bed cut 1501, the ramp region 1502 and pocket region 1503, as well as the pocket depth Dp (measured from the anterior corneal surface), ramp width Wr, and pocket width Wp. Note that the pocket width will be smaller at locations away from the center of the hinge.

Figure 16:
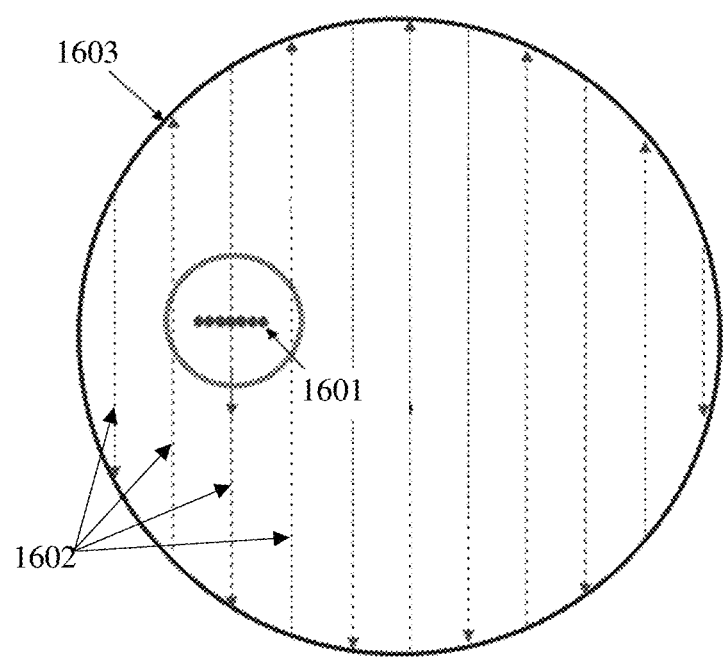
FIG. 16 schematically illustrates a laser scan line generated by an ultrafast raster scanning femtosecond laser and a raster scan pattern using the scan line.

While effective, this cut is difficult to implement with a resonant scanning femtosecond laser. As described in more detail later, and shown in FIG. 16, the laser pulse pattern generated by an ultrafast raster scanning femtosecond laser is in the form of a short laser scan line 1601, which is a line of focused laser pulses formed by the resonant scanner. The scan line 1601 is scanned by the XY scanner in a raster scan movement indicated by arrowed lines 1602, in a direction perpendicular to the scan line in this example, to form the bed cut 1603. Because the scan line 1601 has a fixed width, it is infeasible to use such a scanning scheme to form the arc-shaped ramp and pocket regions shown in FIG. 15.

To solve the problem of excessive bubble formation when cutting a flap bed using an ultrafast raster scanning femtosecond laser, embodiments of the present invention provide a flap cutting procedure, where a pocket is first cut in a region posterior to the intended bed cut surface in a manner that can be conveniently executed by scanning the lase scan line. This pocket is made so that it connects to the bed cut or ring cut and will allow gas bubbles to collect in the pocket rather than collecting at the incision interface of the flap.

Figure 1A:
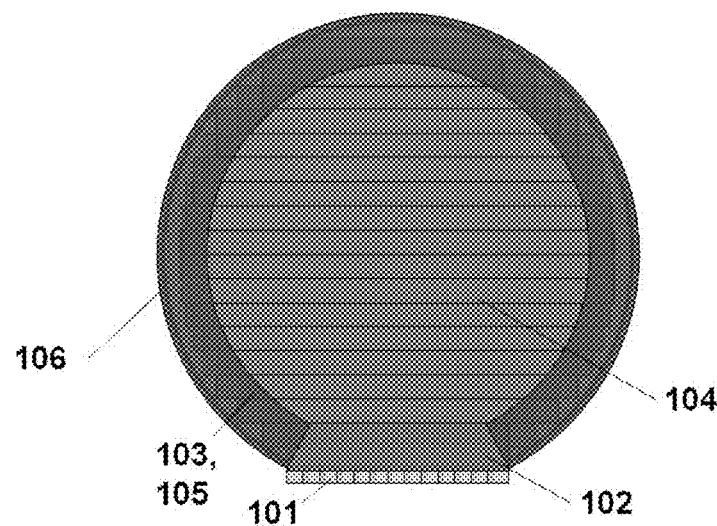
FIGS. 1A and 1B schematically illustrate a flap procedure that forms a corneal flap with a pocket cut according to a first embodiment of the present invention.

FIGS. 1A (top view) and 1B (perspective view) schematically illustrate a flap procedure that forms a corneal flap with a pocket cut according to a first embodiment of the present invention. The flap procedure includes the following components, in the cutting order: a pocket cut 101 with a ramp, a low energy hinge cut 102, a first (low energy) ring cut 103, a bed cut 104, a second (normal energy) ring cut 105, and a side cut 106. The hinge cut 102, ring cuts 103 and 105, and bed cut 104 are located on the same plane, parallel to the anterior corneal surface, to form the bed of the flap. The overall shape of the bed is a circular area except for an uncut arc segment serving as the hinge portion of the flap (the straight line of the arc segment may be referred to as the hinge line). The side cut 106, which extends from the bed upwards to the anterior corneal surface to form the side of the flap, is located around the entire periphery of the bed except for an uncut arc at the hinge. The pocket cut 101 is located at the hinge line of the bed and extends below the bed level.

The pocket cut 101 includes a pocket region 101A and a ramp region 101B. The ramp region 101B is aligned along the hinge line of the flap in the top view, and extends from a depth slightly above the bed level (e.g., 2 to 20 µm above the bed level) to a depth about 70 to 150 µm below the bed level. The pocket region 101A extends substantially horizontally from the lower end of the ramp region 101B for about 150 to 400 µm. The pocket cut 101 preferably extends along the entire length of the hinge line, or along a part of the length of the hinge line. The ramp region 101B may be vertical, or alternatively be inclined (e.g., within 0-170 degrees from the vertical direction). Overall, the pocket cut 101 has a rectangular shape when viewed from the top, and also has a rectangular shape in a side view when viewed along a direction perpendicular to the hinge line.

The cutting sequence is described in more detail with reference to FIGS. 2A1-2B5 (both top and perspective views for each step). The pocket cut 101 is made first, with the ramp region connecting to the bed level of the bed cut to be formed, along the hinge line, as shown in FIGS. 2A1 and 2B1. The pocket cut may be made by placing the laser scan line parallel to the hinge line and scanning the scan line along the intended surface of the pocket cut using the XY scanner and the Z scanner. The scanning direction is radially inwardly for the pocket region 101A and in a deep-to-shallow direction for the ramp region 101B. Multiple passes may be executed side-by-side (preferably with edge overlaps) to form the entire pocket.

Then, a cutting pass is made at the bed level, located across the hinge portion along the hinge line, forming the hinge cut 102 which connects to the pocket cut, as shown in FIGS. 2A2 and 2B2. A low energy ring cut 103 is made at the bed level along the periphery of the bed circle except for the hinge portion, to create the peripheral edge of the flap bed, as shown in FIGS. 2A3 and 2B3. The ring cut 103 is made by placing the laser scan line in a radial direction at the required distance from the center of the bed, so that its outer end is located at the circumference of the bed circle, and scanning the scan line using the XY scanner along the circumferential direction while using the scan line rotator to rotate the scan line direction to keep it in the radial direction. The order of the hinge cut 102 and ring cut 103 may be reversed. Both cuts are made at laser pulse energy levels that are lower than the other cutting steps, e.g., at 90% (or more generally, from 85% to 95%) of the pulse energy of the other cutting steps. These lower energy cuts generate less bubbles and less distortion of the tissue. In preferred embodiments, the pulse energy for the pocket cut, the bed cut, the second ring cut, and the side cut is 40 to 90 nJ.

Figure 4:
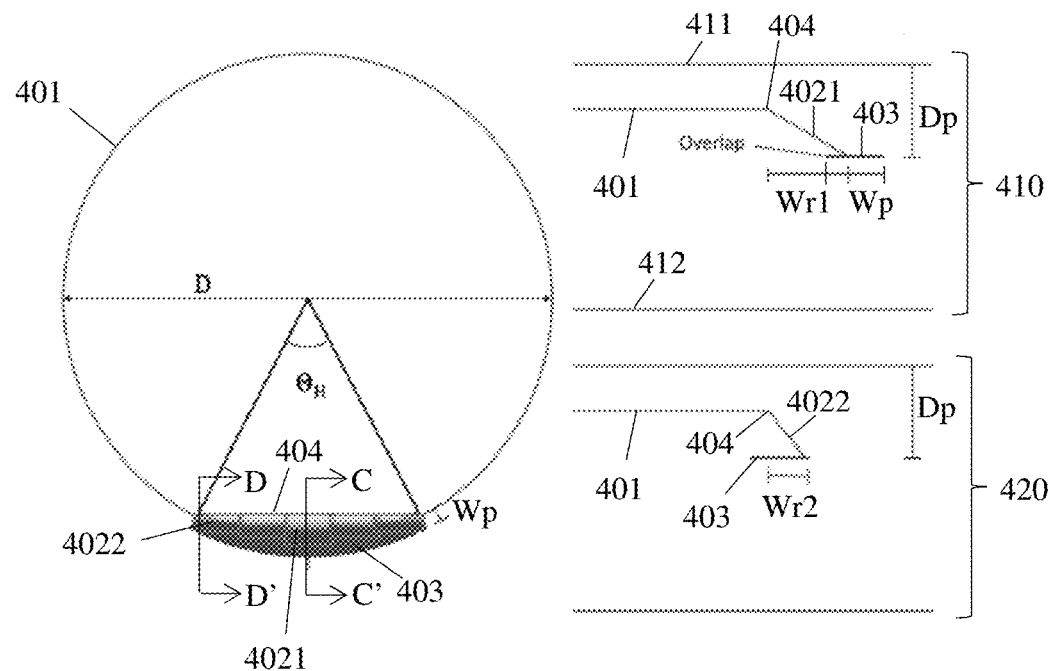
FIG. 4 schematically illustrates a flap procedure that forms a corneal flap with a pocket cut according to a third embodiment of the present invention.
Figure 5:
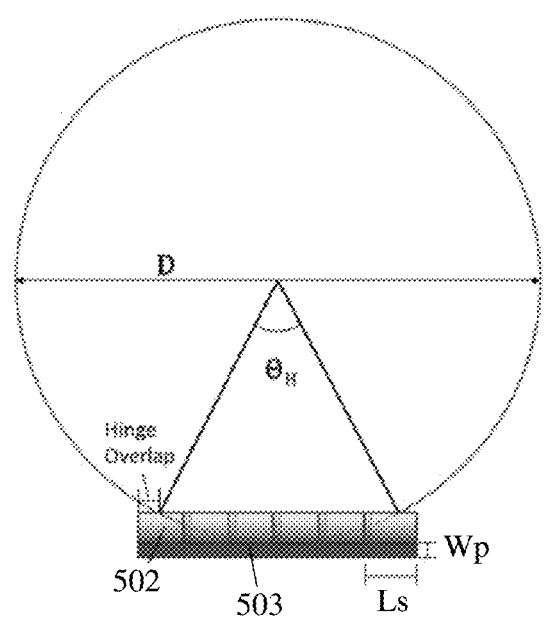

Then, the bed cut 104 is made by creating overlapping parallel raster scan passes of the laser scan line, covering substantially the entire bed circle (at least all the areas not covered by the ring cut 103) except for the arc segment of the hinge, as shown in FIGS. 2A4 and 2B4. Preferably, adjacent parallel raster scan passes overlap with each other in the width direction by at least 50% of their widths, so that in effect, each point is covered by at least two passes. Note that one of the scan passes preferably overlaps with the low energy hinge cut 102. The second ring cut 105 is then made in the same area of the first ring cut 103 to ensure tissue separation at the edges of the bed, as shown in FIGS. 2A5 and 2B5. The second ring cut 105 is made in the same way as the first ring cut 103 but at the normal pulse energy.

The hinge cut 102, first ring cut 103, bed cut 104, and second ring cut 105 overlap each other so that any given point within the bed is covered by at least two passes, which minimize residual uncut tissue bridges. Moreover, the cutting sequence of the hinge cut 102, first ring cut 103, bed cut 104, and second ring cut 105 ensures that a venting channel is always present that connects the current cutting point through earlier-formed cuts to the pocket, so that the gas formed at the current cutting point always has somewhere to escape to, thereby voiding opaque bubble layer formation.

Figure 1B:
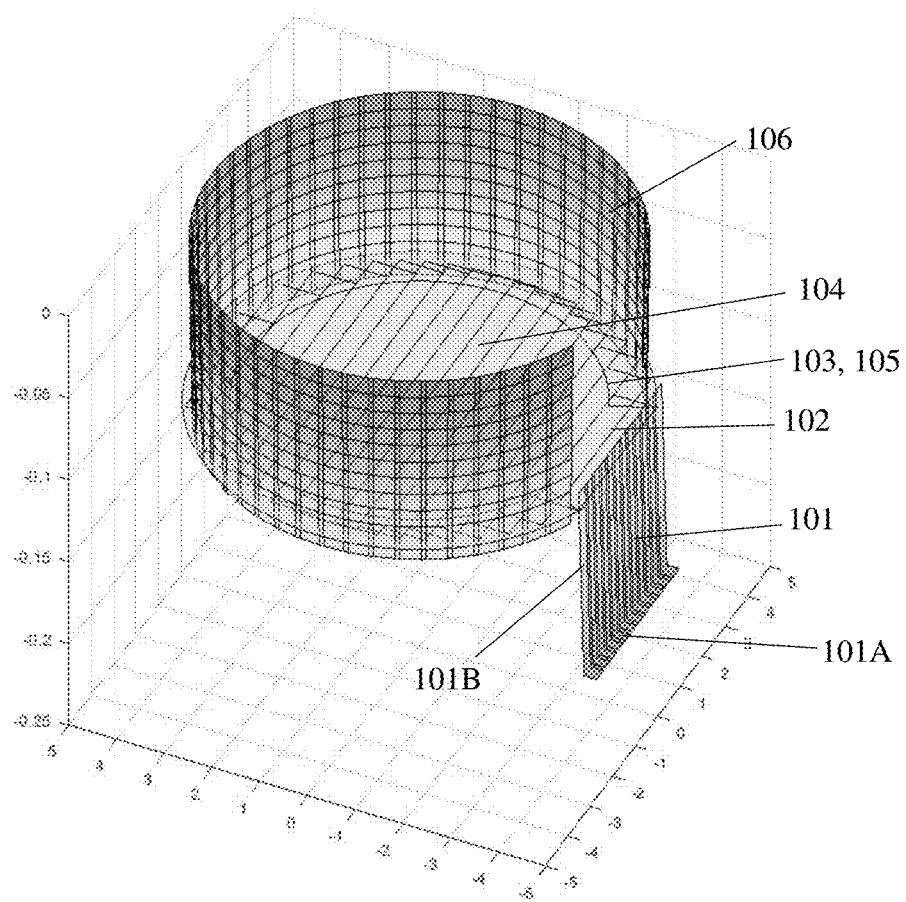

Lastly, a side cut 106 is made, as shown in FIGS. 1A and 1B. The side cut may be formed by placing the laser scan line along the circle of the side cut in a tangential direction, and scanning the scan line in the vertical or near vertical direction using the Z scanner (and optionally the XY scanner) of the ophthalmic laser system. After each vertical scan, the scan line is moved by the XY scanner to the next position along the circle and rotated by the scan line rotator to be again tangent to the circle, and the vertical scanning is repeated. In alternative embodiments, the side cut 106 is formed in using a multilayer technique, described in more detail later.

The cutting order described above, which cuts the ring cut and hinge cut twice, the first time at lower energy, has the advantage of avoiding tissue bridges. Tissue bridges prevent bubbles from traveling to the pocket, and presents problems for flap separation. The low energy hinge cuts 102 and low energy ring cut 103 generate less bubbles and less distortion of tissue.

FIG. 3 (top view and depth profile) schematically illustrates a flap procedure that forms a corneal flap with a pocket cut according to a second embodiment of the present invention. As shown in FIG. 3, the flap is formed of a bed cut 301, which is a circular area except for an uncut arc segment serving as a hinge portion, a pocket cut connected to the bed cut at the hinge, including a ramp region 302 and a pocket region 303, and a vertically extending side cut (also designated by the reference symbol 301) located around the periphery of the bed cut except for the uncut hinge portion. The pocket cut (the ramp region 302 and the pocket region 303 collectively) has a rectangular shape in the top view, with a length L approximately equal to the length of the hinge portion.

FIG. 3 also illustrates a depth profile 310 through the center of the hinge as indicated by arrows B-B', showing the anterior corneal surface 311, posterior corneal surface 312, a part of the bed cut 301, the ramp region 302, and the pocket region 303. As seen in the depth profile, the pocket region 303 is located below (deeper than) the bed cut 301, the upper-inner end of the ramp region 302 is connected to the bed cut 301 at the hinge line 304, and the lower-outer end of the ramp region is connected to the pocket region 303. This way, the ramp region 302 connects the pocket region 303 to the bed 301. In the illustrated embodiments, the depth profile of the ramp 302 is linear, but it may alternatively have a curved shape. For example, it may have rounded connections with the bed cut 301 and with the pocket region 303. FIG. 3 also shows the pocket depth Dp (measured from the anterior corneal surface), ramp width Wr, and pocket width Wp. The depth profile is identical throughout the entire length L of the pocket cut 302/303.

The pocket cut 302/303 is made by placing the laser scan line parallel to the hinge line (i.e., in FIG. 3, the horizontal direction in the top view and the direction perpendicular to the drawing sheet in the depth profile view), and scanning the scan line along the depth profile. Each scan pass starts by placing the scan line at the outer edge of the pocket region at the pocket depth. The XY scanner then moves the scan line at the pocket depth and inwardly (towards the hinge), for the specified pocket width. Then the XY scanner continues to move the scan line inwardly, while the Z scanner moves the depth of the scan line anteriorly, so that the scan line is moved inwardly and upwardly along the ramp region to reach the bed depth at the hinge line. Following a single scan pass, the laser scan line is returned to the pocket depth and another scan pass is made, where the edge of the scan line preferably overlaps with the previous pass. This is repeated until a pocket is made, preferably spanning the entire length of the hinge.

In a particular example, the flap diameter D is 9.0 mm, the pocket width Wp is 250 μm, and the hinge angle $\Theta_H$ is 55°. The scan line length Ls is about 900 μm, and five parallel scans are used to form the entire length of the pocket 302, 303. Other appropriate scan line lengths may be used. More generally, the flap diameter D may be between 5 and 10 mm, the pocket width Wp may be between 150 and 400 μm, and the hinge angle $\Theta_H$ may be between 45 and 90 degrees.

To form the corneal flap in this embodiment, the pocket cut 302, 303 is formed first as described above; then the bed cut and side cut are formed in that sequence, for example using the raster scanning method described in the first embodiment. This flap procedure, including the pocket 302, 303, is design so that it can be made with an ultrafast resonant scanning femtosecond laser.

FIG. 4 (top view and depth profiles) schematically illustrates a flap procedure that forms a corneal flap with a pocket cut according to a third embodiment of the present invention. As shown in FIG. 4, the flap is formed of a bed cut 401, which is a circular area except for an uncut arc segment serving as a hinge portion, a pocket cut connected to the bed cut at the hinge, including a plurality of ramp region segments 4021, 4022 etc. and a pocket region 403, and a vertically extending side cut (also designated by the reference symbol 401) located around the periphery of the bed cut except for the uncut hinge portion. In the top view, each ramp region segment 4021, 4022 etc. is a rectangular shape, and the pocket region 403 is arc shaped band (i.e. a segment of a ring) with a width Wp. In the top view, the pocket region 403 is concentric with the bed cut and overlaps the arc of the hinge portion.

FIG. 4 also shows a depth profile 410 through the center of the hinge as indicated by arrows C-C', and a depth profile 420 through a location near the end of the hinge as indicated by arrows D-D'. The depth profiles shows the anterior corneal surface 411, posterior corneal surface 412, a part of the bed cut 401, the ramp region segments 4021 and 4022 respectively, and the pocket region 403. As seen in the depth profiles, the pocket region 403 is located below (deeper than) the bed cut at pocket depth Dp (measured from the anterior corneal surface); at different locations along the arc (e.g., center vs. end), the pocket region 403 is at different distances from the hinge line 404, due to the arc shape of the pocket region. Each ramp region segment 4021, 4022, etc. is connected at its upper-inner end to the bed cut 401 at the hinge line 404, and connected at its lower-outer end to the pocket region 403. This way, the ramp region segments 4021, 4022, etc. connect the pocket region 403 to the bed 401. As seen in the two representative depth profiles 410 and 420, the ramp region segments 4021, 4022 span between the same bed depth and the same pocket depth, but have different slopes (hence different ramp widths Wr1 and Wr2) so that they reach the pocket region at the appropriate locations. In other words, the different ramp regions are not connected with each other, but they are all connected to the pocket region and to the bed cut at the hinge line 404. Similar to the embodiment of FIG. 3, the depth profile of each ramp region may have a linear or non-linear shape.

The pocket region cut 403 is made by scanning the laser scan line in a similar manner as forming the ring cut in the first embodiment, but the scan line is located at the pocket depth and the required distance from the center of the bed circle, and the scan spans only the required angular range. Each ramp region segment 4021, 4022, etc. is made by placing the laser scan line parallel to the hinge line, and scanning the scan line along the depth profile of that tamp region in a similar manner as forming the ramp region in the second embodiment. As indicated earlier, different ramp regions start at different positions and have different slopes. In one example, the laser scan line is set to approximately 400 μm long when cutting the pocket region, and set to 900 μm long when cutting each ramp region; five ramp regions are formed by five scan passes, as illustrated in FIG. 4. Other appropriate scan line lengths may be used.

The values of the flap diameter D, pocket width Wp, and hinge angle $\Theta_H$ are similar to those in the second embodiment.

To form the corneal flap in this embodiment, the pocket region is formed first, followed by the ramp regions to connect the pocket region to the bed level. Then the bed cut and side cut are formed in that sequence, for example using the raster scanning method described in the first embodiment. This flap procedure, including the pocket and ramps, is design so that it can be made with an ultrafast resonant scanning femtosecond laser.

FIG. 5 (top view) schematically illustrates a flap procedure that forms a corneal flap with a pocket cut according to a fourth embodiment of the present invention. This flap procedure is similar to that of the second embodiment (FIG. 3), except that the length of the ramp region 502 and pocket region 503 extend past the edges of the hinge as indicated by the hinge overlap area in FIG. 5. The pocket region and ramp region may be formed using the same technique described in the second embodiment.

Figure 6:
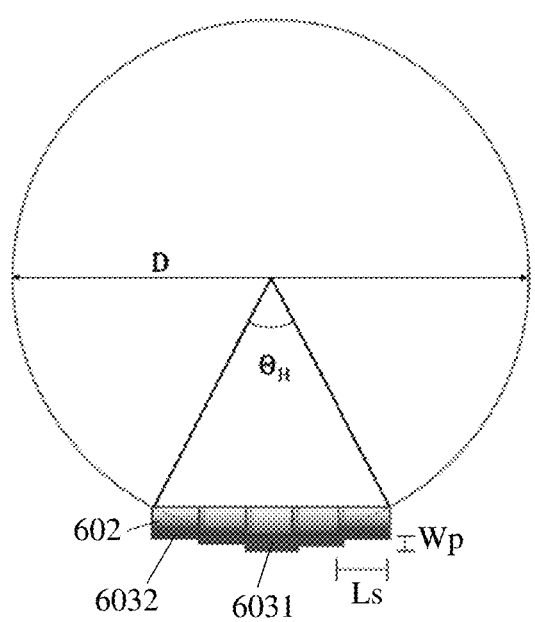
FIG. 6 schematically illustrates a flap procedure that forms a corneal flap with a pocket cut according to a fifth embodiment of the present invention.

FIG. 6 (top view) schematically illustrates a flap procedure that forms a corneal flap with a pocket cut according to a fifth embodiment of the present invention. This flap procedure is similar to that of the second embodiment (FIG. 3), except that the width of the different pocket regions 6031, 6032, etc. are different, where the pocket region 6031 at the center of the hinge has the largest width Wp and the pocket region 6032 at the end of the hinge has the smallest width. The pocket regions 6031, 6302, etc. are located at the same depth, and the ramp region 602 has the same slope throughout. The pocket regions and ramp region may be formed using the same technique described in the second embodiment.

In alternative embodiments (not shown in the drawings), the pocket region and ramp region in the second embodiment (FIG. 3) and the fourth embodiment (FIG. 5) may be made in a different scan method. In these alternative embodiments, the pocked region 303 or 503 is still formed in the same manner described earlier, but the ramp region 302 or 502 is formed by a single scan of the laser scan line moving in a direction parallel to the hinge. More specifically, the resonant scanner scans the laser focal spot in a direction perpendicular to the hinge, and simultaneously, the Z scanner moves the laser focal spot up and down at the same frequency of the resonant scanner and synchronized with the same phase with the resonant scanner, to form a tilted scan line that extends between the bed and the pocket region. In the side view, the scan line has the same shape as the ramp 302 shown in FIG. 3. This scan line is scanned in a direction parallel to the hinge line by the XY scanner.

In other alternative embodiments, the ramp region 302 or 502 is still formed in the same manner described earlier, but the pocked region 303 or 503 is formed by a single scan of the laser scan line placed at the pocket level and perpendicular to the hinge, and moved in a direction parallel to the hinge.

Figure 7A:
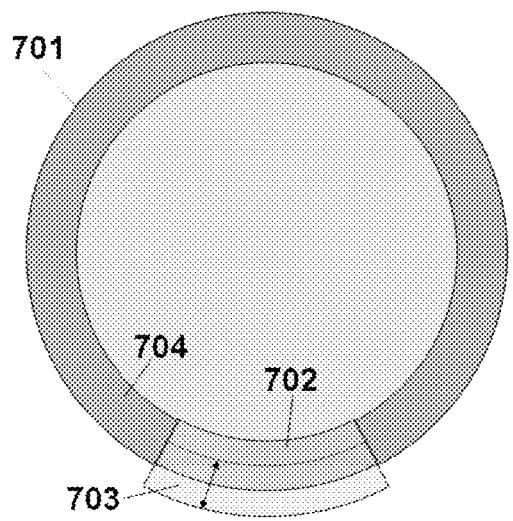
FIGS. 7A-7B schematically illustrate a flap procedure that forms a corneal flap with a pocket cut according to a sixth embodiment of the present invention.
Figure 7B:
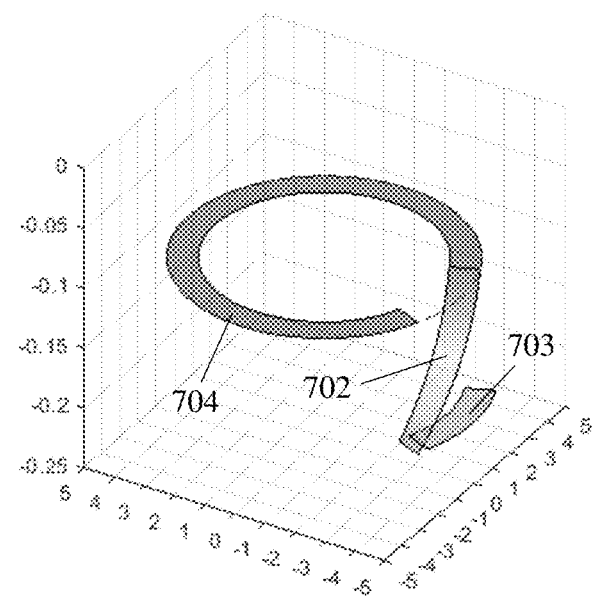

FIGS. 7A (top view) and 7B (perspective view) schematically illustrate a flap procedure that forms a corneal flap with a pocket cut according to a sixth embodiment of the present invention. The flap is formed of a bed cut 701, which is a circular area except for an uncut arc segment serving as a hinge portion, a pocket cut connected to the bed cut, including a ramp region 702 and a pocket region 703, and a vertically extending side cut (also designated by the reference symbol 701 in FIG. 7A, but not shown in FIG. 7B) located around the periphery of the bed cut except for the uncut hinge portion. The bed cut 701 includes a ring cut 704 similar to the ring cut 103 or 105 in the first embodiment shown in FIGS. 1A and 1B.

The pocket region 703 is located at a level below the bed level and has the shape of a segment of a ring in the top view, concentric with the bed and located approximately within the hinge portion. In the illustrated embodiment, the inner and outer radii of the pocket region 703 are respectively larger than the inner and outer radii of the ring cut 704 (the pocket width is indicated by the double-arrowed line), but this is not required. The pocket region 703 is made by scanning a laser scan line along an arc at the pocket level in a manner similar to forming the pocket region 403 in the third embodiment shown in FIG. 4.

In some embodiment, the pocket region 703 may be formed in a two-pass scan, starting from the center of the hinge portion (and outsider of the bed area) and moving counter-clockwise (or clockwise) in the first pass, and then moving in the clockwise (or counter-clockwise) direction from one end of the hinge portion to the other end in the second pass.

The ramp region 702 connects the pocket region 703 to the ring cut 704 at the bed level. In the top view, the ramp region 702 has the shape of a segment of a ring, concentric with the ring cut and having the same inner and outer radii (and hence the same width) as the ring cut, and located within the hinge portion. The two circumferential ends of the ramp region 702 are respectively connected to the pocket region 703 and the ring cut 704. The ramp region 702 is formed by placing the laser scan line in a radial direction, at a location near one end of the pocket region 703 but at a depth slightly below the pocket region to ensure connectivity. The scan line is then moved by the XY scanner along an arc toward the other end of the hinge region, simultaneously rotated by the scan line rotator to keep it in the radial direction, and simultaneously moved by the Z scanner upwards toward the bed level, to a position where it connects with a circumferential end of the ring cut at the bed level (see FIG. 7B).

To form the corneal flap in this embodiment, the pocket region 703 is formed first, followed by the ramp region 702, then by the bed cut (including the ring cut) and then the side cut using the method described earlier. This flap procedure is design so that it can be made with an ultrafast resonant scanning femtosecond laser.

Figure 8A:
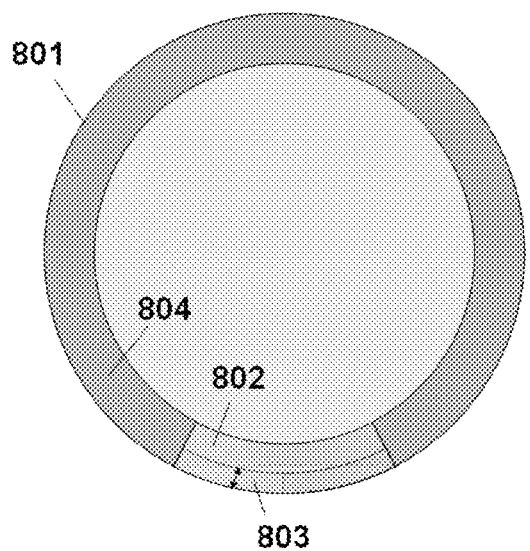
FIGS. 8A-8B schematically illustrate a flap procedure that forms a corneal flap with a pocket cut according to a seventh embodiment of the present invention.

FIGS. 8A (top view) and 8B (perspective view) schematically illustrate a flap procedure that forms a corneal flap with a pocket cut according to a seventh embodiment of the present invention. This embodiment is similar to the sixth embodiment (FIGS. 7A-7B), except that the pocket width (as indicated by the double-arrowed line) is narrower. In this example, the inner radius of the pocket region 803 is still larger than the inner radius of the ring cut 804, but the outer radius of the pocket region 803 is approximately the same as the outer radius of the ring cut 804. The pocket region 803 is formed in a similar manner as the pocket region 703 in the sixth embodiment, but the length the laser scan line is shorter. The bed 801, ring cut 804 and ramp region 802 are the same as in the sixth embodiment.

Figure 8B:
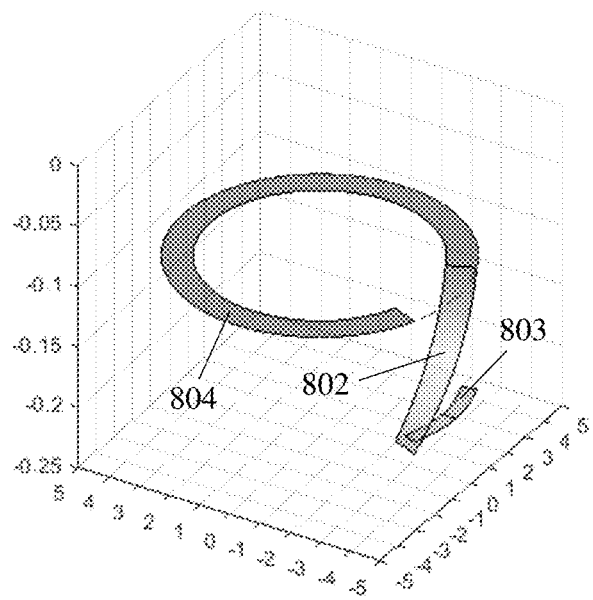
Figure 9A:
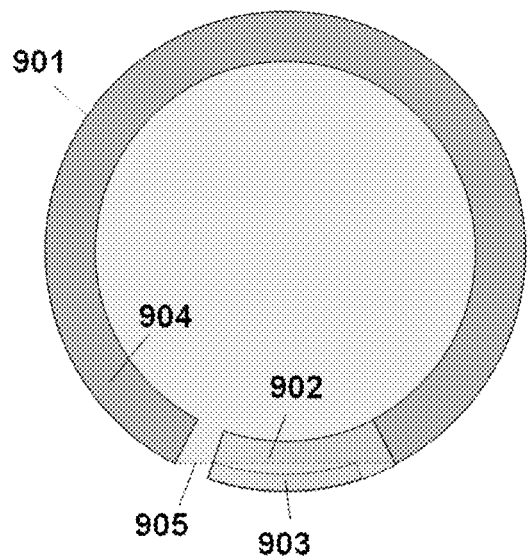
FIGS. 9A-9B schematically illustrate a flap procedure that forms a corneal flap with a pocket cut according to an eighth embodiment of the present invention.
Figure 9B:
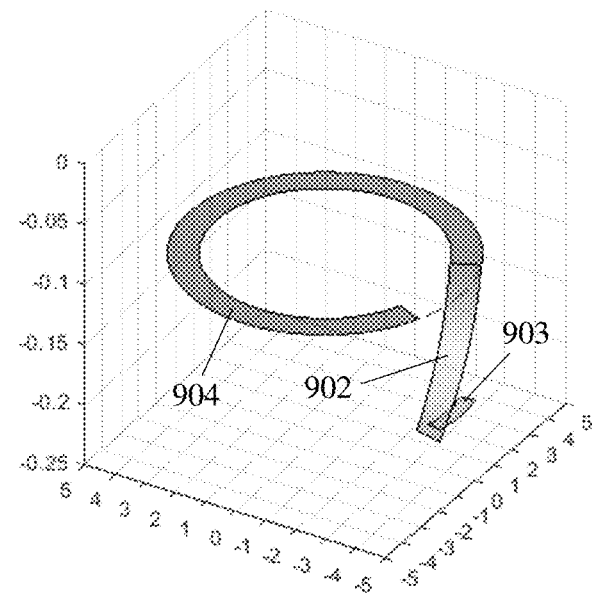

FIGS. 9A (top view) and 9B (perspective view) schematically illustrate a flap procedure that forms a corneal flap with a pocket cut according to an eighth embodiment of the present invention. This embodiment is similar to the seventh embodiment (FIGS. 8A-8B), except that the pocket region and the ramp region do not extend across the entire range of the hinge region in the top view. Similar to the embodiment in FIG. 8A, the pocket region 903 has an inner radius that is larger than the inner radius of the ring cut. The pocket region 903 does not reach either end of the hinge region, and lies entirely outside of the bed area, i.e., outside of the hinge line 905. The ramp region 902 is ramped to connect the pocket region 903 to the ring cut 904, but is shorter in the top view as compared to the ramp regions 702 and 802 of the sixth and seventh embodiments. The pocket region 903 and ramp region 902 are formed in similar manners as the pocket region and ramp region in the sixth and seventh embodiments. The bed 901 and ring cut 904 are the same as in the sixth and seventh embodiments.

Figure 10A:
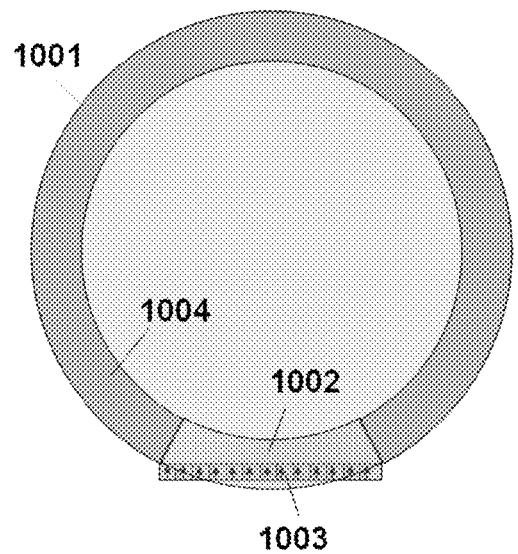
FIGS. 10A-10B schematically illustrate a flap procedure that forms a corneal flap with a pocket cut according to a ninth embodiment of the present invention.
Figure 10B:
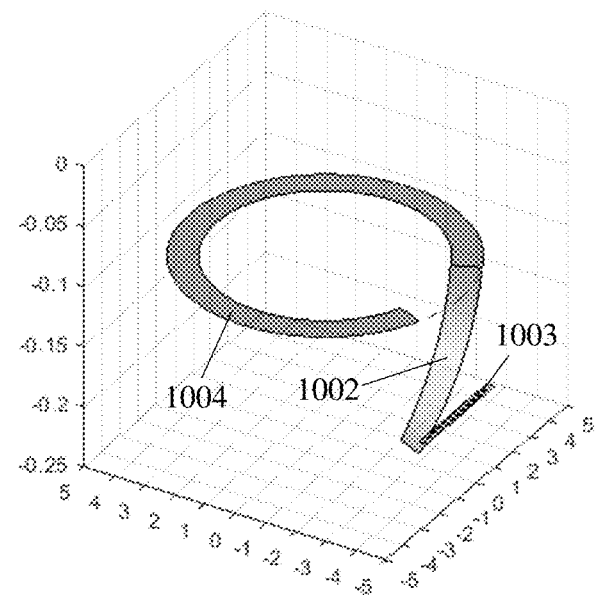

FIGS. 10A (top view) and 10B (perspective view) schematically illustrate a flap procedure that forms a corneal flap with a pocket cut according to a ninth embodiment of the present invention. This embodiment is similar to the sixth and seventh embodiments except for the pocket region. Rather than a ring segment, the pocket region 1003 is a rectangle in the top view, located in the hinge region but outside of the hinge line. The pocket region 1003 may be formed by scanning the laser scan line in multiple passes, where in each pass the laser scan line is placed at the pocket level parallel to the hinge line and scanned inwardly. Alternatively (not shown), the pocket region 1003 may be formed by a single scan pass, by placing the laser scan line at the pocket level perpendicular to the hinge line and scanning it in a direction parallel to the hinge line. The bed 1001, ring cut 1004 and the ramp region 1002 are the same as in the sixth and seventh embodiments.

FIGS. 11A (top view) and 11B (perspective view) schematically illustrate a flap procedure that forms a corneal flap with a pocket cut according to a tenth embodiment of the present invention. The pocket region 1103 in this embodiment is a rectangle in the top view, located within the hinge region but outside of the hinge line. It may be formed by multiple scan passes of a single scan pass (shown in FIG. 11A), similar to the pocket region 1003 of the ninth embodiment. The ramp regions 1102 in this embodiment is similar to those of the sixth to ninth embodiments in that it connects to a circumferential end of the ring cut 1104, but the ramp region does not strictly follow the circumferential direction of the bed in the top view. Rather, in the top view, the ramp region is shaped like a part of a spiral band, which deviate slightly from the circle defined by the ring cut, such that the lower end of the ramp region is located outside of the circle of the ring cut, in order to properly connect with the pocket region 1103. Again, the cutting is performed in the sequence of the pocket region, the ramp region, the bed cut, and the side cut.

It can be seen that in the first to fifth embodiments (FIG. 1A-6), the ramp region is connected to the bed along the hinge line, and in the second to fifth embodiments, the ramp region slopes upward as it extends in the lateral direction perpendicular to the hinge line; in the sixth to tenth embodiments (FIGS. 7A-11B), the ramp region is connected to the bed at a circumferential end of the ring cut (at one end of the hinge region), and the ramp region slopes upward as it extends in the circumferential direction of the flap.

In the first to tenth embodiments described above, the pocket depth Dp is comparable to flap thickness (i.e. the bed depth), such as from 0.5 to 1.5 times the flap thickness.

In each embodiment, one or more of the following parameters may be varied: laser scan line length for both the pocket and ramp, pocket width, scan line overlaps, pocket depth, bed depth, and cutting order.

In the flap cutting procedures according to the above embodiments, the pockets allow the gas bubbles to move into the pockets and out of the laser path of the subsequent cut. It is not essential for the bubbles to move all the way back to the pocket, however, so long as they move backward to earlier cut areas. Thus, for example, in a ring, bed, side cut cutting order, when cutting the side cut, it is not essential for the gas bubbles to move into the pocket; rather, it is sufficient if they move back to the ring or bed cut.

FIG. 12 (perspective view) schematically illustrates a flap procedure that forms a corneal flap according to an eleventh embodiment of the present invention which employs a layered side cut. Again, all segment of the flap cut are created using a scan line generated using the resonant scanner.

In conventional flap procedures, the flap cut is executed by forming a ring cut (at the bed level) first, followed by a side cut, then by a bed cut. The side cut is a single layer which is created by moving the laser scan line sinusoidally in Z and XY directions between the top of the side cut (at or slightly above anterior corneal surface) and the bottom of the side cut (at or slightly below the bed level), tangent to the side-cut path (the circle in the top view). One problem with this side cut method is that, because the scan line reaches the anterior corneal surface in each sinusoidal period of the scan, gas bubbles generated during the cut will escape from cornea and be trapped between the cornea and the patient interface lens; such gas bubbles may move sideways into a center areas of the flap, which may interfere with the subsequent bed cut. The patient interface is a device used to mechanically couple the patient's eye to the laser surgical system; the patient interface typically has a lens that contacts and applanates the cornea during the procedure.

In the flap procedure according to the eleventh embodiment of the present invention, the cutting sequence is to form a bed 1201 first, which includes a ring cut and a bed cut executed in either order, then form a side cut 1202 after the bed is completed. Moreover, the side cut 1202 is formed using a multi-layer technique.

More specifically, the side cut 1202 is formed one layer at a time, where each layer 1202-1, 1202-2, 1202-3, etc. is a part of the overall side cut but extends only in a depth range that is a sub-range of the entire depth range of the side cut. All but the top layer are completely located within the cornea and do not reach the anterior corneal surface. The layers are aligned with each other along the entire depth range and connect with each other to form the side cut. The adjacent layers preferably overlap each other in the depth direction (i.e., their sub-ranges overlap each other). In one example, the layer thickness, i.e. the size of the depth sub-range, is about 25 µm, and the overlap between two adjacent layers is about 10 µm. More generally, the layer thickness may be from 10 to 40 µm, and the layer overlap may be from 2 to 15 µm. The bottom-most layer may extend below the bed level and the top-most layer may extend above the anterior corneal surface, to ensure proper separation of the flap. The number of side cut layers is determined by the total depth of the side cut, the thickness of each layer and the amount of overlap between adjacent layers. The example illustrated in FIG. 12 has eight layers. The different layers may also have different thicknesses.

The side cut layers are formed in a sequence from posterior to anterior (i.e. deeper to shallower relative to the anterior corneal surface), preferably changing layers at the corner of the hinge to start the subsequent side cut layer. The top of the last side cut layer that is located completely inside the cornea is preferably within less than 20 µm from the top surface of epithelium in order to manage the bubbles generated within the ring cut, bed cut and side cut.

The side cut may be perpendicular to the anterior corneal surface, or at a non-right angle relative to the anterior corneal surface.

Figure 13:
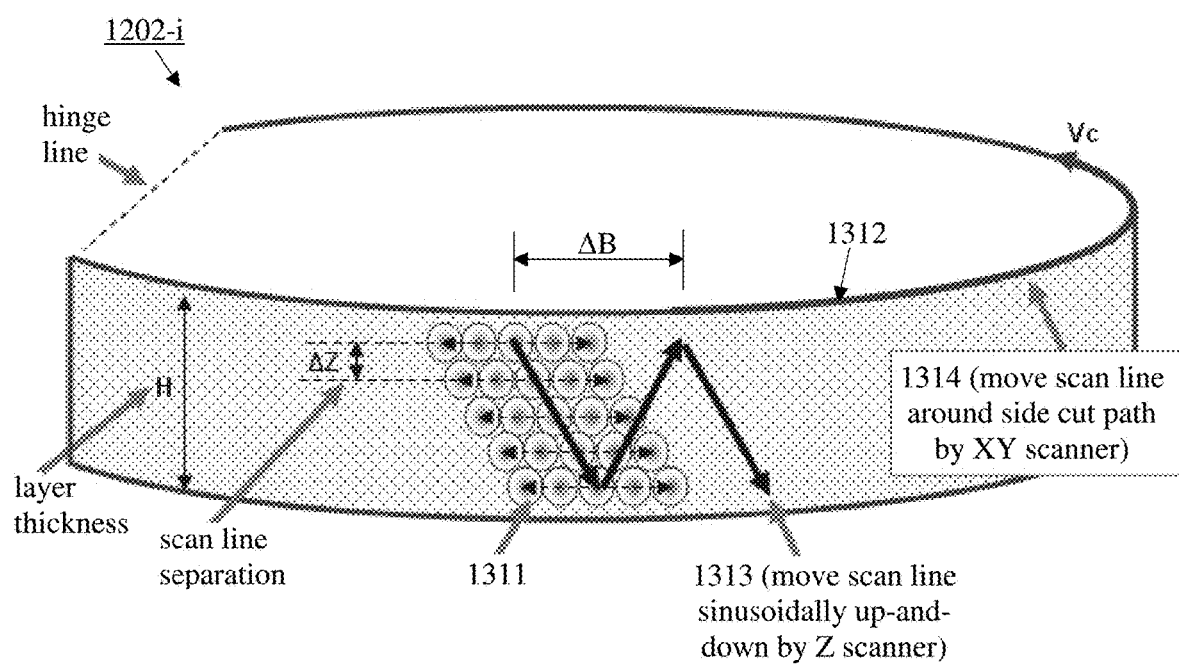
FIG. 13 schematically illustrates a step of forming a layer of the side cut in the eleventh embodiment.
Figure 14:
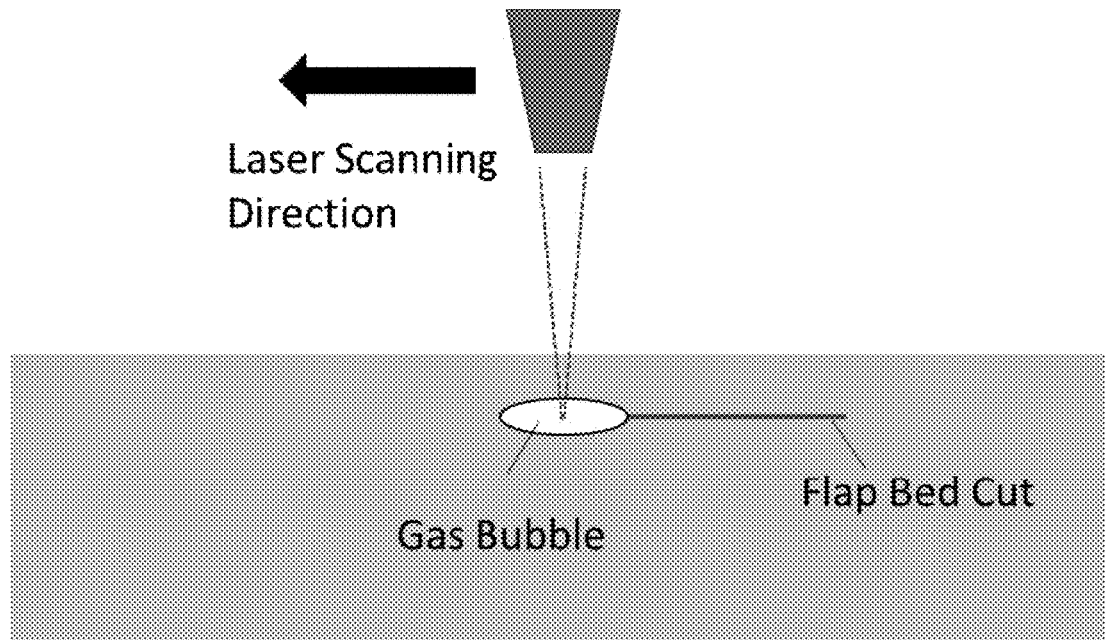
FIG. 14 schematically illustrates a flap bed cut being formed in the tissue and a gas bubble that was created by the laser during a previous laser raster scan.

As shown in FIGS. 13, each side cut layer 1202-i is created by placing the laser scan line 1311 (shown as 1211 in FIG. 12) tangent to the side-cut path (along the circumference) 1312, moving it sinusoidally in the Z direction 1313, simultaneously moving it around the side-cut path in the circumferential XY direction 1314, and simultaneously rotating the scan line to keep it tangent to the side-cut path. The depth Z of the scan line as a function of time (measured from the center depth of the layer) is given by:

$$Z(t) = \frac{H}{2}\sin(2\pi \cdot f_z \cdot t), \ f_z = \frac{\Delta_z}{H}f_s, \ V_c = \Delta B \cdot f_z$$

where H is the layer thickness, $f_z$ is the Z scan frequency, $f_s$ is the resonant scan frequency that produces the scan line, $\Delta_z$ is a scan line-to-line separation parameter, H is the layer thickness, $V_c$ is the speed of the XY scan in the circumferential direction, and $\Delta B$ is a band-to-band separation of the band in the circumferential direction in one period of the Z scan. Preferably, during the anterior to posterior half of each sinusoidal period, the laser beam is fast blanked, e.g. blocked by using an acousto-optic modulator of the laser system, in order to manage the generated bubbles in the corneal tissue.

In one particular example for creating the layered side cut, the Z scan frequency was 120 Hz, the scan line length was 600 µm, the scan line overlap was 25%, the glass overcut at the anterior corneal surface was 90 µm, the side cut angle was 120°, and the flap diameter was 8.0 mm.

In the embodiment of FIG. 12, the ring cut and bed cut are similar to the ring cut 105 and bed cut 104 in the first embodiment (FIGS. 1A and 1B). Although not shown in FIG. 12, a pocket may be created below the bed cut using a method according to any of the preceding embodiments.

In embodiments of the present invention described above, the execution sequences for the various cuts that form the pocket, the flap bed and flap side ensure that a venting channel is always present that connects the current cutting point through earlier-formed cuts to the bottom part of the pocket, so that the gas formed at the current cutting point always has somewhere to escape to, thereby voiding opaque bubble layer formation.

Figure 17A:
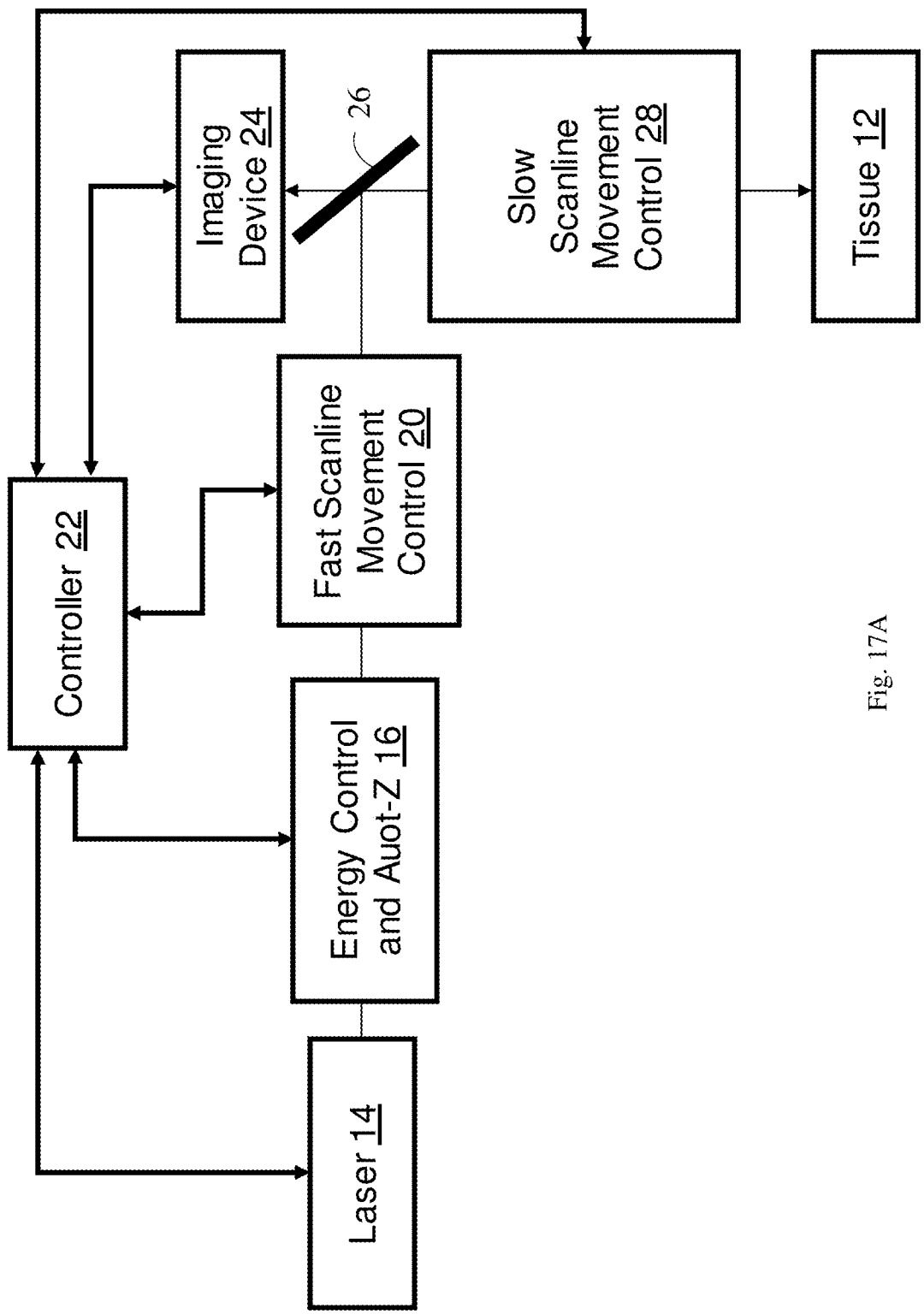
FIGS. 17A and 17B schematically illustrate two exemplary ophthalmic laser systems which may be used to implement embodiments of the present invention.
Figure 17B:
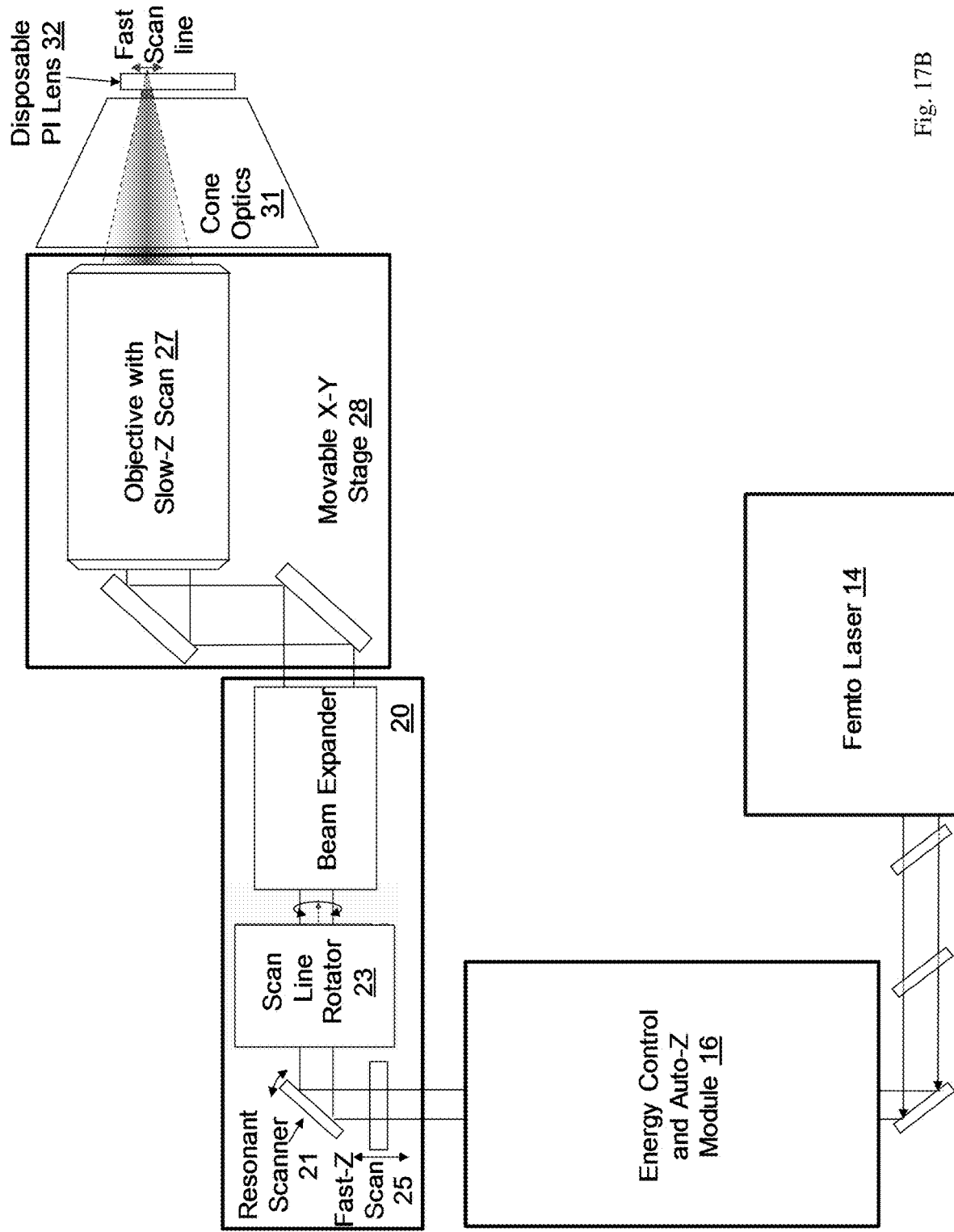

Ophthalmic laser systems that may be used to implement the above-described flap formation procedures are described in more detail now with reference to FIGS. 17A and 17B.

FIG. 17A shows a system 10 for making an incision in a tissue 12 of a patient's eye, such as a cornea. The system 10 includes, but is not limited to, a laser 14 capable of generating a pulsed laser beam, an energy control module 16 for varying the pulse energy of the pulsed laser beam, a fast scan line movement control module 20 for generating the scan line of the pulsed laser beam, a controller 22, and a slow scan line movement control module 28 for moving the laser scan line and delivering it to the tissue 12. The controller 22, such as a processor operating suitable control software, is operatively coupled with the fast scan line movement control module 20, the slow scan line movement control module 28, and the energy control module 16 to direct the scan line of the pulsed laser beam along a scan pattern on or in the tissue 12. In this embodiment, the system 10 further includes a beam splitter 26 and a imaging device 24 coupled to the controller 22 for a feedback control mechanism (not shown) of the pulsed laser beam. Other feedback methods may also be used. In an embodiment, the pattern of pulses may be summarized in machine readable data of tangible storage media in the form of a treatment table. The treatment table may be adjusted according to feedback input into the controller 22 from an automated image analysis system in response to feedback data provided from a monitoring system feedback system (not shown).

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the tissue or other material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver a near infrared laser beam comprising a plurality of laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam toward an eye (for example, onto or into a cornea) for plasma mediated photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam toward the eye.

FIG. 17B shows another exemplary diagram of the laser system 10. FIG. 17B shows components of a laser delivery system including a moveable XY-scanner (or movable XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 40-100 nJ range and pulse repetitive rates (or "rep rates") in the 2-40 MHz range. A fast-Z scanner 25 and a resonant scanner 21 direct the laser beam to a scan line rotator 23. When used in an ophthalmic procedure, the system 10 also includes a patient interface design that has a fixed cone nose 31 and a contact lens 32 that engages with the patient's eye. A beam splitter may be placed inside the cone 31 of the patient interface to allow the whole eye to be imaged via visualization optics. In some embodiments, the system 10 may use: optics with a 0.6 numerical aperture (NA) which would produce 1.1 µm Full Width at Half Maximum (FWHM) focus spot size; and a resonant scanner 21 that produces 0.2-1.2 mm scan line with the XY-scanner scanning the resonant scan line to a 1.0 mm field. The scan line rotator 23 (e.g., a Dove or Pechan prism, a set of mirrors, or the like, mounted on a rotating stage) rotates the resonant scan line to any direction on the XY plane. The fast-Z scanner 25 sets the incision depth. The slow scan line movement control module employs a movable XY-stage 28 carrying an objective lens with Z-scanning capability 27, referred to as slow-Z scanner because it is slower than the fast-Z scanner 25. The movable XY-stage 28 moves the objective lens to achieve scanning of the laser scan line in the X and Y directions. The objective lens changes the depth of the laser scan line in the tissue. The energy control and auto-Z module 16 may include appropriate components to control the laser pulse energy, including attenuators, etc. It may also include an auto-Z module which employs a confocal or non-confocal imaging system to provide a depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

In preferred embodiments, the beam scanning can be realized with a "fast-scan-slow-sweep" scanning scheme, also referred herein as a fast-scan line scheme. The scheme consists of two scanning mechanisms: first, a high frequency fast scanner (e.g., the resonant scanner 21 of FIG. 17B) is used to scan the beam back and forth to produce a short, fast scan line; second, the fast scan line is slowly swept by much slower X, Y, and Z scan mechanisms (e.g. the moveable X-Y stage 28 and the objective lens with slow-Z scan 27, and the fast-Z scanner 25). For example, the laser system may use an 8 kHz (e.g. between 7 kHz and 9 kHz, or more generally, between 0.5 kHz and 20 kHz) resonant scanner 21 to produce a fast scan line of about 1 mm (e.g., between 0.9 mm and 1.1 mm, or more generally, between 0.2 mm and 1.2 mm) and a scan speed of about 25 m/sec, and X, Y, and Z scan mechanisms with the scan speed (sweeping speed) smaller than about 0.1 m/sec. The fast scan line may be perpendicular to the optical beam propagation direction, i.e., it is always parallel to the XY plane. The trajectory of the slow sweep can be any three dimensional curve drawn by the X, Y, and Z scanning devices (e.g., XY-scanner 28 and fast-Z scanner 25). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

As described earlier, the flap procedures in various embodiments of the present invention utilize the fast-scan-slow-sweep scanning scheme to form various cuts of the flap. The controller of the laser system controls the various components of the system to form the above-described cuts.

It will be apparent to those skilled in the art that various modification and variations can be made in the corneal flap procedure and related apparatus of the present invention without departing from the spirit or scope of the invention. Thus, it is intended that the present invention cover modifications and variations that come within the scope of the appended claims and their equivalents.

What is claimed is:

1. An ophthalmic surgical laser system for incising a cornea of a patient's eye to form a corneal flap, comprising:
   a laser delivery system configured to deliver a pulsed laser beam to the cornea;
   a high frequency scanner configured to scan the pulsed laser beam back and forth to form a laser scan line in the cornea;
   a scan line rotator configured to rotate a direction of the laser scan line in a transverse plane perpendicular to a depth direction;
   an XY-scanner configured to move a position of the laser scan line in the transverse plane;
   a Z-scanner configured to move the laser scan line in the depth direction; and
   a controller programmed to control the laser delivery system, the high frequency scanner, the scan line rotator, the XY-scanner and the Z-scanner to form the corneal flap, including to form a pocket cut, a bed of the flap, and a side cut of the flap,
   wherein the bed is located in a horizontal plane at a first depth from an anterior corneal surface, the bed defining a hinge line,
   wherein the side cut extends from the bed upwards to the anterior corneal surface to form a side of the flap, the side cut surrounding an entire periphery of the bed except the hinge line,
   wherein the pocket cut includes a ramp region and a pocket region connected to each other, wherein the pocket region is located at a second depth from the anterior corneal surface which is deeper than the first depth, wherein the pocked region has a shape of a rectangle, or multiple rectangles joined to each other, or a segment of a ring in a top view, and wherein the ramp region extends between the first depth and the second depth and is connected to both the bed and the pocket region, and
   wherein the pocket cut is formed first, the bed is formed after the pocket cut, and the side cut is formed after the bed.

2. The system of claim 1, wherein the controller is programmed to form the bed by: forming a hinge cut along the hinge line by scanning the laser scan line along the hinge line; forming a first ring cut along a periphery of the bed except for an area of the hinge cut by scanning the laser scan line along a circumference of the bed; forming a bed cut by scanning the laser scan line in overlapping parallel raster scan passes, the bed cut overlapping at least a part of the hinge cut and the first ring cut and covering all areas of the bed not covered by the hinge cut and the first ring cut; and forming a second ring cut overlapping the first ring cut by scanning the laser scan line along the circumference of the bed.

3. The system of claim 1, wherein the pocket region has a shape of a rectangle or multiple rectangles joined to each other in the top view, wherein the pocket region is formed in multiple passes, and each pass includes placing the laser scan line at the second depth parallel to the hinge line and scanning the laser scan line horizontally in a direction perpendicular to the hinge line.

4. The system of claim 1, wherein the pocket region has a shape of a rectangle in the top view and is formed by placing the laser scan line at the second depth perpendicular to the hinge line, and scanning the laser scan line horizontally in a direction parallel to the hinge line.

5. The system of claim 1, wherein the pocket region has an arc shaped in the top view and is formed by placing the laser scan line at the second depth and parallel to a radial direction of the bed, and scanning the laser scan line horizontally in a circumferential direction of the bed.

6. The system of claim 1, wherein the ramp region is connected to the bed along the hinge line and extends in a vertical direction, wherein the ramp region is formed in multiple passes, and each pass includes placing the laser scan line in a direction parallel to the hinge line and scanning the laser scan line vertically.

7. The system of claim 1, wherein the ramp region is connected to the bed along the hinge line, the ramp region sloping upward as it extends in a lateral direction toward the hinge line, wherein the ramp region is formed in multiple passes, and each pass includes placing the laser scan line in a direction parallel to the hinge line and scanning the laser scan line simultaneously in a horizontal direction perpendicular to the hinge line and in a vertical direction.

8. The of claim 1, wherein the ramp region includes a plurality of segments each connected to the bed along the hinge line, wherein each ramp region segment slopes upward as it extends in a lateral direction toward the hinge line, wherein at least some of the ramp region segments have different slopes, and wherein each ramp region segment is formed by placing the laser scan line in a direction parallel to the hinge line and scanning the laser scan line simultaneously in a horizontal direction perpendicular to the hinge line and in a vertical direction.

9. The of claim 1, wherein the ramp region is connected to the bed at a circumferential end of a ring shaped region of the bed, wherein the ramp region slopes upward as it extends in a circumferential direction of the bed, and wherein the ramp region is formed by placing the laser scan line parallel to a radial direction of the bed and scanning the laser scan line simultaneously in a horizontal and circumferential direction of the bed and in a vertical direction.

10. An ophthalmic surgical laser system for incising a cornea of a patient's eye to form a corneal flap, comprising:
    a laser delivery system configured to deliver a pulsed laser beam to the cornea;
    a high frequency scanner configured to scan the pulsed laser beam back and forth to form a laser scan line in the cornea;
    a scan line rotator configured to rotate a direction of the laser scan line in a transverse plane perpendicular to a depth direction;
    an XY-scanner configured to move a position of the laser scan line in the transverse plane;
    a Z-scanner configured to move the laser scan line in the depth direction; and
    a controller programmed to control the laser delivery system, the high frequency scanner, the scan line rotator, the XY-scanner and the Z-scanner to form the corneal flap, including to form a bed of the flap and a side cut of the flap,
    wherein the bed is located in a horizontal plane at a first depth from an anterior corneal surface, the bed defining a hinge line, wherein the side cut extends from the bed upwards to the anterior corneal surface to form a side of the flap, the side cut surrounding an entire periphery of the bed except for the hinge line, and
    wherein the controller is programmed to form the bed by:
        forming a hinge cut along the hinge line by scanning the laser scan line along the hinge line;
        forming a first ring cut along a periphery of the bed except for an area of the hinge cut by scanning the laser scan line along a circumference of the bed;
        forming a bed cut by scanning the laser scan line in overlapping parallel raster scan passes, the bed cut overlapping at least a part of the hinge cut and the first ring cut and covering all areas of the bed not covered by the hinge cut and the first ring cut; and
        forming a second ring cut overlapping the first ring cut by scanning the laser scan line along the circumference of the bed.

11. The system of claim 10, wherein the side cut is formed after the bed.

12. The system of claim 10, wherein the bed cut is formed after both the hinge cut and the first ring cut, and the second ring cut is formed after the bed cut.

13. The system of claim 10, wherein the hinge cut and the first ring cut are formed using a first laser pulse energy, and the bed cut, the second ring cut, and the side cut are formed using a second laser pulse energy which is higher than the first laser pulse energy.

14. The system of claim 13, wherein the first laser pulse energy is 85% to 95% of the second laser pulse energy.

15. The system of claim 13, wherein the controller is programmed to form the corneal flap by further forming a pocket cut located below the bed and connected to the bed, wherein the bed is formed after the pocket cut and the side cut is formed after the bed, and wherein the pocket cut is formed using the second laser pulse energy.

16. An ophthalmic surgical laser system for incising a cornea of a patient's eye to form a corneal flap, comprising:
    a laser delivery system configured to deliver a pulsed laser beam to the cornea;
    a high frequency scanner configured to scan the pulsed laser beam back and forth to form a laser scan line in the cornea;
    a scan line rotator configured to rotate a direction of the laser scan line in a transverse plane perpendicular to a depth direction;
    an XY-scanner configured to move a position of the laser scan line in the transverse plane;
    a Z-scanner configured to move the laser scan line in the depth direction; and
    a controller programmed to control the laser delivery system, the high frequency scanner, the scan line rotator, the XY-scanner and the Z-scanner to form the corneal flap, including to form a bed of the flap and a side cut of the flap,
    wherein the bed is located in a horizontal plane parallel to an anterior corneal surface of the cornea, wherein the side cut extends from the bed upwards to the anterior corneal surface to form a side of the flap, and
    wherein the controller is programmed to form the side cut by forming a plurality of side cut layers in a sequence, each side cut layer extending within a depth range from the anterior corneal surface, wherein all except one of the plurality of side cut layers are located entirely within the cornea without reaching the anterior corneal surface, and wherein the plurality of side cut layers are aligned with each other and connect with each other to form the side cut, and
    wherein the plurality of side cut layers are formed in a sequence from deeper side cut layers to shallower side cut layers.

17. The system of claim 16, wherein the depth ranges of adjacent side cut layers overlap each other.

18. The system of claim 16, wherein each of the plurality of side cut layers is formed by placing the laser scan line tangent to a circumference of the side cut, moving the laser scan line in a vertical direction, simultaneously moving the laser scan line around the circumference, and simultaneously rotating the scan line to keep it tangent to the circumference.

* * * * *